(12) United States Patent
Mason

(10) Patent No.: US 7,881,503 B2
(45) Date of Patent: Feb. 1, 2011

(54) CORNEAL BIOMETRY APPARATUS AND METHOD

(75) Inventor: Stephen A. Mason, Collaroy (AU)

(73) Assignee: Positive Eye-D Ltd, Sydney, NSW (AU)

( * ) Notice: Subject to any disclaimer, the term of this patent is extended or adjusted under 35 U.S.C. 154(b) by 852 days.

(21) Appl. No.: 11/576,031

(22) PCT Filed: Sep. 12, 2005

(86) PCT No.: PCT/AU2005/001386

§ 371 (c)(1),
(2), (4) Date: Aug. 2, 2007

(87) PCT Pub. No.: WO2006/034527

PCT Pub. Date: Apr. 6, 2006

(65) Prior Publication Data

US 2007/0291997 A1    Dec. 20, 2007

Related U.S. Application Data

(60) Provisional application No. 60/685,484, filed on May 31, 2005.

(30) Foreign Application Priority Data

Sep. 29, 2004    (AU) ............................... 2004905635

(51) Int. Cl.
*G06K 9/00* (2006.01)
*A61B 3/14* (2006.01)
*A61B 3/10* (2006.01)

(52) U.S. Cl. ...................... 382/115; 382/117; 351/206; 351/212

(58) Field of Classification Search ................ 382/117, 382/115, 100; 351/212, 209, 246, 221, 160 R, 351/162, 205, 161, 206, 211, 247, 177, 210; 606/1, 2, 4, 5, 107; 600/300, 398; 604/19, 604/20, 28, 35; 514/385, 912, 706; 424/78.04, 424/78.02
See application file for complete search history.

(56) References Cited

U.S. PATENT DOCUMENTS

| | | | | |
|---|---|---|---|---|
| 5,644,642 | A * | 7/1997 | Kirschbaum | 382/103 |
| 5,757,461 | A * | 5/1998 | Kasahara et al. | 351/206 |
| 6,271,915 | B1 * | 8/2001 | Frey et al. | 356/124 |
| 7,275,827 | B2 * | 10/2007 | Jean et al. | 351/212 |
| 2001/0054149 | A1 * | 12/2001 | Kawaguchi et al. | 713/175 |
| 2003/0144650 | A1 * | 7/2003 | Smith | 606/5 |
| 2003/0169213 | A1 * | 9/2003 | Spero | 345/7 |
| 2005/0024586 | A1 * | 2/2005 | Teiwes et al. | 351/209 |
| 2006/0210122 | A1 | 9/2006 | Cleveland et al. | |

FOREIGN PATENT DOCUMENTS

JP    2005211631    8/2005

* cited by examiner

*Primary Examiner*—Sheela C Chawan
(74) *Attorney, Agent, or Firm*—Molins & Co

(57) ABSTRACT

An apparatus and method for validating the identity of a person using corneal imaging techniques. The method involves capturing an image of at least part of a person's cornea and deriving one or more geometric parameters. The geometric parameters are compared with corresponding reference geometric parameters for validation of the identity of the person.

26 Claims, 13 Drawing Sheets

| vs 1130 | AXL | DST | HGT | SLP | TCL | Total |
|---|---|---|---|---|---|---|
| Total Difference | 0.09675935 | 0.00380464 | -0.00173683 | -0.00037496 | 0.01698269 | 0.72% |
| Total Difference (%) | 0.07 | 0.18 | 0.18 | 0.06 | 0.24 | |
| Valid | 8283 / 9568 | 8611 / 9600 | 8611 / 9600 | 8611 / 9600 | 8311 / 9600 | |
| Valid (%) | 86.6 | 89.7 | 89.7 | 89.7 | 86.6 | |
| Abs. Diff (1-6) | 61.50057634 | 3.82850459 | 0.25591730 | 0.22886554 | 163.2612283 | 229.0961719 |
| Abs. Diff (7-12) | 27.74471714 | 4.24672006 | 0.86255722 | 0.65638339 | 178.6905798 | 212.2008796 |
| Abs. Diff (13-18) | 31.60796791 | 9.11186274 | 3.07920994 | 1.54364193 | 228.4643911 | 273.8070735 |
| Abs. Diff (19-24) | 62.83767282 | 38.10476653 | 16.55182421 | 4.73414410 | 534.0886456 | 656.3157634 |
| Abs. Diff (25-30) | 44.74060806 | 40.10527920 | 22.54962096 | 4.45435304 | 548.2662117 | 660.1380729 |
| Abs. Diff (All) | 228.4315422 | 95.39592292 | 43.29915143 | 11.61728806 | 1652.813454 | 2031.558961 |

| vs 114 | AXL | DST | HGT | SLP | TGL | Total |
|---|---|---|---|---|---|---|
| Total Difference | -0.35712575 | -0.07931324 | 0.00643527 | -0.00300752 | -0.20529799 | -12.99% |
| Total Difference (%) | -4.39 | -3.51 | -2.72 | 0.92 | -3.30 | |
| Valid | 7637 / 9568 | 8164 / 9600 | 8164 / 9600 | 8164 / 9600 | 7865 / 9600 | |
| Valid (%) | 81.9 | 85.0 | 85.0 | 85.0 | 81.9 | |
| Abs. Diff (1-6) | 600.0296315 | 32.61845634 | 1.33935566 | 0.61943114 | 680.6882589 | 1315.295613 |
| Abs. Diff (7-12) | 673.1590049 | 97.23426635 | 7.81098372 | 2.40035567 | 821.5241873 | 1602.128798 |
| Abs. Diff (13-18) | 769.3163105 | 180.0198950 | 24.65332237 | 6.05676631 | 1058.521859 | 2038.768134 |
| Abs. Diff (19-24) | 566.4753079 | 200.7507705 | 43.01492236 | 11.30258695 | 1489.544592 | 2311.088187 |
| Abs. Diff (25-30) | 218.5743357 | 116.5919287 | 40.04645794 | 7.27300220 | 1827.793276 | 2210.279001 |
| Abs. Diff (All) | 2827.554590 | 627.2153250 | 117.0658220 | 27.65214128 | 5878.072155 | 9477.559735 |

Figure 4

|  | Tot Dif | Tot Dif % | Valid | Valid % | Dif 1-6 | Dif 7-12 | Dif 13-18 | Dif 19-24 | Dif 25-30 | Dif - All |
|---|---|---|---|---|---|---|---|---|---|---|
|  | 1 -0.416669 | -5.03 | 8086 / 956 | 84.5 | 516.202 | 561.7184 | 711.7519 | 890.8668 | 661.2586 | 3341.798 |
|  | 10 -0.287573 | -3.49 | 7744 / 956 | 80.9 | 453.5101 | 518.1518 | 535.6239 | 480.091 | 278.6257 | 2266.003 |
|  | 100 -0.003712 | 0 | 8182 / 956 | 85.5 | 171.7988 | 113.9062 | 208.0762 | 335.0754 | 258.3391 | 1087.196 |
|  | 101 -0.08348 | -1.01 | 7785 / 956 | 81.4 | 256.6202 | 244.7672 | 277.9317 | 265.6128 | 179.1421 | 1224.074 |
|  | 102 -0.685428 | -8.37 | 7690 / 956 | 80.4 | 1186.585 | 1165.797 | 1211.641 | 1070.844 | 614.8956 | 5249.762 |
|  | 103 -0.809672 | -9.81 | 8133 / 956 | 85 | 1220.659 | 1278.428 | 1363.47 | 1595.777 | 1077.629 | 6535.963 |
|  | 104 -0.367211 | -4.45 | 8282 / 956 | 86.6 | 555.9375 | 613.7563 | 654.562 | 759.2134 | 443.8429 | 3027.312 |
|  | 105 -0.726862 | -8.85 | 7994 / 956 | 83.5 | 992.6885 | 1132.731 | 1383.064 | 1410.106 | 851.7993 | 5770.388 |
|  | 106 -0.444352 | -5.43 | 7846 / 956 | 82 | 766.081 | 711.7446 | 797.5797 | 751.3514 | 470.5808 | 3497.337 |
|  | 107 -0.635861 | -7.69 | 8422 / 956 | 88 | 940.2777 | 997.9694 | 1089.122 | 1330.62 | 951.8547 | 5309.845 |
|  | 108 -0.536906 | -6.59 | 7338 / 956 | 76.7 | 717.3436 | 875.3271 | 959.4925 | 877.7887 | 479.2883 | 3909.24 |
|  | 109 -0.405496 | -4.89 | 8326 / 956 | 87 | 584.1198 | 638.3425 | 719.5582 | 894.9692 | 546.8303 | 3383.82 |
|  | 11 -0.417208 | -5.04 | 8047 / 956 | 84.1 | 561.9223 | 620.9018 | 716.0154 | 925.5567 | 514.9947 | 3339.391 |
|  | 110 -0.579938 | -7.05 | 8297 / 956 | 86.7 | 887.5325 | 1004.016 | 1037.712 | 1144.349 | 710.9329 | 4784.542 |
|  | 110 -0.617071 | -7.48 | 8271 / 956 | 86.4 | 948.0689 | 984.1201 | 1067.346 | 1274.936 | 805.3895 | 5079.86 |
|  | 112 -0.43134 | -5.17 | 8422 / 956 | 88 | 584.5144 | 606.3294 | 653.8784 | 939.8075 | 804.5012 | 3589.031 |
| 113B | 0.005759 | 0.07 | 8283 / 956 | 86.6 | 61.50058 | 27.74472 | 31.60797 | 62.83767 | 44.74061 | 228.4315 |
| 113C | 0.003074 | 0.04 | 8316 / 956 | 86.9 | 47.57969 | 20.32774 | 21.62535 | 36.73575 | 31.5967 | 157.8652 |
|  | 114 -0.357126 | -4.39 | 7837 / 956 | 81.9 | 600.0296 | 673.159 | 769.3163 | 566.4753 | 218.5743 | 2827.555 |
|  | 115 -0.232904 | -2.78 | 8374 / 956 | 87.5 | 288.7349 | 264.9293 | 379.0869 | 604.4374 | 438.7918 | 1975.98 |
|  | 116 -0.71545 | -8.66 | 7952 / 956 | 83.1 | 1029.388 | 1108.713 | 1214.87 | 1433.339 | 867.6714 | 5651.981 |
|  | 117 -0.141358 | -1.66 | 8364 / 956 | 87.4 | 162.5376 | 163.4143 | 276.0598 | 491.4991 | 330.051 | 1423.562 |
|  | 118 -0.439406 | -5.29 | 8235 / 956 | 86.1 | 495.5735 | 640.0882 | 806.5466 | 1000.657 | 650.1306 | 3592.996 |
|  | 119 0.080947 | 1.06 | 7536 / 956 | 78.8 | 288.8289 | 269.5442 | 239.8216 | 321.1056 | 324.5037 | 1443.804 |
|  | 12 0.131907 | 1.72 | 7595 / 956 | 79.4 | 551.7218 | 500.6435 | 338.6675 | 259.4596 | 242.4874 | 1892.98 |
| 120A | -0.202801 | -2.41 | 8154 / 956 | 85.2 | 271.2168 | 272.5615 | 338.3876 | 595.0648 | 317.2017 | 1794.432 |
| 120B | -0.198449 | -2.35 | 8109 / 956 | 84.8 | 242.9939 | 224.8153 | 343.8143 | 587.8673 | 305.9925 | 1705.483 |
|  | 121 -0.18369 | -2.2 | 7931 / 956 | 82.9 | 170.1137 | 243.4842 | 421.9484 | 553.0397 | 236.5873 | 1625.173 |
|  | 122 -0.269114 | -3.24 | 8264 / 956 | 86.4 | 324.345 | 428.906 | 504.8273 | 632.0029 | 334.7468 | 2224.828 |
|  | 123 -0.379083 | -4.57 | 8149 / 956 | 85.2 | 517.8838 | 533.5381 | 612.3937 | 810.1242 | 604.865 | 3078.805 |
|  | 124 -0.097825 | -1.18 | 8097 / 956 | 84.6 | 194.5977 | 196.4455 | 225.3045 | 270.8508 | 209.307 | 1096.505 |
|  | 125 -0.787347 | -9.61 | 8029 / 956 | 83.9 | 1276.288 | 1367.841 | 1427.881 | 1480.028 | 743.6616 | 6295.699 |
|  | 126 -0.542441 | -6.62 | 8116 / 956 | 84.8 | 919.4304 | 990.0558 | 1023.164 | 1032.459 | 422.8055 | 4387.914 |
|  | 127 -0.079745 | -0.93 | 7597 / 956 | 79.4 | 129.5881 | 143.2715 | 211.1439 | 264.8514 | 162.157 | 911.0118 |
|  | 128 -0.359454 | -4.39 | 7584 / 956 | 79.3 | 522.9727 | 606.003 | 688.4244 | 658.7809 | 258.6781 | 2734.859 |
|  | 129 -0.364506 | -4.37 | 8348 / 956 | 87.2 | 448.8412 | 478.2909 | 561.2258 | 784.8191 | 746.1235 | 3019.3 |
|  | 13 -0.205873 | -2.44 | 8311 / 956 | 86.9 | 355.8455 | 381.6166 | 444.1501 | 662.0623 | 475.9538 | 2319.628 |
|  | 130 -0.405962 | -4.98 | 6901 / 956 | 72.1 | 495.6964 | 597.3587 | 603.3711 | 602.4701 | 482.1162 | 2781.013 |
|  | 131 -0.184859 | -2.15 | 8192 / 956 | 85.6 | 165.4119 | 196.8947 | 377.3286 | 636.6874 | 467.3831 | 1843.706 |
|  | 132 -0.590656 | -7.2 | 7964 / 956 | 83.2 | 952.6699 | 998.4798 | 1071.185 | 1078.047 | 603.7111 | 4704.093 |
|  | 133 -0.713165 | -8.69 | 8157 / 956 | 85.3 | 1163.581 | 1221.682 | 1247.975 | 1360.648 | 797.3086 | 5791.194 |
|  | 134 -0.207669 | -2.47 | 7728 / 956 | 80.8 | 237.5459 | 289.5829 | 382.8256 | 482.5423 | 391.9878 | 1784.484 |
|  | 135 -0.112717 | -1.35 | 8093 / 956 | 84.6 | 149.7804 | 168.964 | 250.8303 | 382.2834 | 271.0126 | 1222.871 |
|  | 136 -0.273691 | -3.29 | 8395 / 956 | 87.7 | 391.976 | 355.7279 | 431.0483 | 645.5608 | 493.5135 | 2317.827 |
|  | 137 -0.038628 | -0.44 | 7008 / 956 | 73.2 | 205.0934 | 244.5282 | 200.0768 | 180.723 | 113.7448 | 944.1663 |
|  | 138 -0.186107 | -2.22 | 7978 / 956 | 83.4 | 206.329 | 201.9609 | 380.09 | 584.7759 | 324.5481 | 1697.704 |
|  | 139 -0.748132 | -9.17 | 7693 / 956 | 80.4 | 1307.633 | 1209.184 | 1347.998 | 1413.03 | 504.9331 | 5782.779 |
|  | 14 -0.482476 | -5.83 | 8259 / 956 | 86.3 | 667.0625 | 741.5809 | 841.668 | 1023.729 | 674.459 | 3948.499 |
|  | 140 -0.311329 | -3.77 | 7977 / 956 | 83.4 | 438.0572 | 506.839 | 585.6287 | 654.0228 | 301.1921 | 2485.74 |
|  | 141 -0.504518 | -6.06 | 8325 / 956 | 87 | 556.8872 | 681.5918 | 856.0374 | 1211.761 | 860.9049 | 4167.183 |
|  | 142 0.716077 | 8.95 | 7546 / 956 | 78.9 | 1998.329 | 1633.229 | 1183.19 | 561.7731 | 247.6065 | 5624.128 |
|  | 143 -0.181566 | -2.17 | 8230 / 956 | 86 | 309.426 | 391.4192 | 457.7713 | 287.6315 | 1748.431 |
|  | 144 -0.456451 | -5.55 | 8208 / 956 | 85.8 | 602.0736 | 649.2244 | 767.4399 | 1030.23 | 675.7076 | 3724.675 |
|  | 145 -0.722681 | -8.72 | 8406 / 956 | 87.9 | 932.7552 | 1056.648 | 1200.73 | 1568.067 | 1244.952 | 6003.152 |
|  | 146 -0.356995 | -4.35 | 7601 / 956 | 79.4 | 678.1861 | 667.304 | 608.4775 | 519.4104 | 421.5583 | 2894.936 |
|  | 147 0.047217 | 0.59 | 7634 / 956 | 79.8 | 241.5753 | 227.5895 | 241.2848 | 262.3826 | 120.1834 | 1093.016 |
|  | 148 -0.579742 | -7.01 | 8418 / 956 | 88 | 785.8665 | 863.3242 | 931.6873 | 1221.713 | 981.9649 | 4834.556 |
|  | 149 -0.762891 | -9.3 | 8064 / 956 | 84.3 | 1218.71 | 1284.951 | 1359.625 | 1366.127 | 881.522 | 6110.935 |
|  | 15 -0.486947 | -5.86 | 8313 / 956 | 86.9 | 616.0327 | 710.9231 | 875.0939 | 1118.209 | 719.6325 | 4039.891 |
|  | 150 -0.002069 | 0.02 | 8049 / 956 | 84.1 | 197.0904 | 162.0701 | 194.2409 | 257.5355 | 158.7104 | 969.6473 |
|  | 151 -0.152776 | -1.82 | 8027 / 956 | 83.9 | 222.3377 | 220.8885 | 276.2331 | 354.2949 | 245.7716 | 1319.526 |
|  | 152 -0.34216 | -4.11 | 8368 / 956 | 87.5 | 385.7544 | 467.8766 | 588.1019 | 845.5618 | 573.4184 | 2860.713 |
| 153A | -0.780154 | -9.53 | 7790 / 956 | 81.4 | 1248.315 | 1291.734 | 1370.55 | 1335.491 | 796.5834 | 6042.674 |
| 153B | -0.196223 | -2.32 | 8158 / 956 | 85.3 | 317.3746 | 227.8687 | 271.2685 | 532.5561 | 504.8292 | 1853.897 |

Figure 5

|  | Tot Dif | Tot Dif % | Valid | Valid % | Dif 1-6 | Dif 7-12 | Dif 13-18 | Dif 19-24 | Dif 25-30 | Dif - All |
|---|---|---|---|---|---|---|---|---|---|---|
| 154 | -0.481965 | -5.87 | 8161 / 956 | 85.3 | 825.7021 | 816.3431 | 845.4768 | 961.5122 | 488.9483 | 3937.982 |
| 155 | -0.379376 | -4.55 | 8353 / 956 | 87.3 | 419.9777 | 496.1932 | 618.5539 | 940.0015 | 686.384 | 3161.11 |
| 156 | -0.759455 | -9.26 | 8033 / 956 | 84 | 1101.954 | 1248.083 | 1409.629 | 1411.719 | 920.5062 | 6091.891 |
| 157 | -0.283594 | -3.42 | 7893 / 956 | 82.5 | 414.1127 | 434.5029 | 444.9247 | 733.8343 | 362.5458 | 2389.92 |
| 158 | -0.526778 | -6.4 | 8307 / 956 | 86.8 | 799.5928 | 842.7145 | 957.1391 | 1098.782 | 650.2273 | 4348.456 |
| 158 | -0.033651 | -0.38 | 7707 / 956 | 80.5 | 132.1964 | 150.5522 | 217.4391 | 288.1796 | 179.6961 | 968.0634 |
| 159 | -0.269193 | -3.19 | 8399 / 956 | 87.8 | 215.8229 | 278.066 | 392.5686 | 705.101 | 676.708 | 2268.267 |
| 159 | -0.517598 | -6.28 | 8133 / 956 | 85 | 706.0585 | 786.1928 | 907.6958 | 1068.163 | 714.4583 | 4180.568 |
| 16 | 0.040143 | 0.51 | 7897 / 956 | 82.5 | 161.1938 | 150.0741 | 194.6241 | 274.0028 | 184.0806 | 963.9755 |
| 160 | -0.48974 | -5.93 | 8110 / 956 | 84.8 | 723.3582 | 756.2873 | 830.0297 | 961.2912 | 681.6654 | 3952.632 |
| 161 | -0.284349 | -3.44 | 8177 / 956 | 85.5 | 372.9706 | 528.691 | 584.4912 | 670.3833 | 255.5306 | 2412.067 |
| 162 | -1.147522 | -13.98 | 8229 / 956 | 86 | 1878.651 | 1951.902 | 2020.758 | 2170.14 | 1368.135 | 9389.586 |
| 163 | -0.199411 | -2.36 | 8418 / 956 | 88 | 196.8471 | 211.6513 | 320.0672 | 530.4129 | 456.02 | 1714.999 |
| 164 | -0.219144 | -2.65 | 7532 / 956 | 78.7 | 282.0757 | 330.2377 | 437.868 | 309.4446 | 298.7833 | 1658.409 |
| 165 | -0.544675 | -6.7 | 7865 / 956 | 82.2 | 952.4712 | 941.6315 | 1071.674 | 927.9833 | 475.0463 | 4368.807 |
| 166 | -0.362466 | -4.36 | 8201 / 956 | 85.7 | 470.9272 | 549.7538 | 664.8031 | 798.4993 | 489.2588 | 2973.242 |
| 167 | -0.428502 | -5.2 | 8034 / 956 | 84 | 571.4151 | 645.646 | 763.0496 | 882.407 | 565.8152 | 3428.333 |
| 168 | -0.34856 | -4.22 | 8178 / 956 | 85.5 | 536.5845 | 611.7149 | 607.8368 | 721.368 | 372.7408 | 2850.245 |
| 169 | -0.705869 | -8.6 | 7867 / 956 | 82.2 | 1091.012 | 1155.299 | 1257.361 | 1254.173 | 755.1403 | 5512.985 |
| 17 | -0.162509 | -1.95 | 7592 / 956 | 79.3 | 220.7826 | 239.9823 | 309.2841 | 293.9908 | 230.1715 | 1294.211 |
| 170 | -0.840768 | -7.86 | 7345 / 956 | 76.8 | 982.9157 | 1042.366 | 1169.494 | 1020.543 | 462.7602 | 4678.079 |
| 171 | -0.304868 | -3.72 | 7536 / 956 | 78.8 | 409.6855 | 509.8917 | 594.0068 | 446.633 | 326.239 | 2286.456 |
| 172 | -0.311197 | -3.75 | 7629 / 956 | 79.7 | 352.3146 | 401.0406 | 542.6768 | 554.2202 | 503.7531 | 2354.005 |
| 173 | -0.339334 | -4.19 | 6466 / 956 | 67.6 | 466.0845 | 577.1769 | 525.3106 | 399.3784 | 184.6816 | 2172.632 |
| 174 | 0.11792 | 1.45 | 7071 / 956 | 73.9 | 210.5481 | 199.7808 | 206.9341 | 178.6987 | 148.9696 | 944.9313 |
| 175A | -0.144116 | -1.74 | 7743 / 956 | 80.9 | 223.3422 | 250.7306 | 291.7959 | 340.5873 | 187.9674 | 1294.423 |
| 175B | -0.14346 | -1.73 | 7873 / 956 | 82.3 | 228.7572 | 248.8406 | 282.666 | 367.5755 | 209.7264 | 1337.566 |
| 175C | -0.163336 | -1.97 | 7712 / 956 | 80.6 | 253.5282 | 262.9672 | 304.9931 | 363.6319 | 215.3085 | 1400.429 |
| 175D | -0.158943 | -1.91 | 8015 / 956 | 83.8 | 236.704 | 259.412 | 296.0647 | 402.8371 | 255.8694 | 1450.887 |
| 175E | -0.161396 | -1.95 | 7785 / 956 | 81.4 | 246.9682 | 263.6974 | 306.5012 | 365.2086 | 211.0146 | 1393.39 |
| 176 | -0.233823 | -2.81 | 7944 / 956 | 83 | 326.5225 | 376.8177 | 439.7524 | 467.6905 | 436.0937 | 2047.077 |
| 177 | -0.400307 | -4.88 | 8350 / 956 | 87.3 | 793.6892 | 682.5722 | 723.4026 | 964.3135 | 487.0229 | 3651 |
| 178 | -0.363286 | -4.39 | 7920 / 956 | 82.8 | 536.7269 | 548.2105 | 624.8969 | 746.0449 | 462.9898 | 2918.869 |
| 179 | -0.179905 | -2.17 | 8067 / 956 | 84.3 | 217.6464 | 225.7838 | 332.9316 | 480.3537 | 298.0985 | 1554.814 |
| 18 | -1.972067 | -24.41 | 7578 / 956 | 79.2 | 3612.304 | 4183.618 | 3948.723 | 2348.606 | 851.3192 | 14944.57 |
| 180 | -0.121553 | -1.4 | 7960 / 956 | 83.2 | 144.8058 | 109.576 | 182.7586 | 480.0814 | 310.6983 | 1227.92 |
| 181 | -0.581471 | -7.07 | 8118 / 956 | 84.8 | 938.6542 | 934.5697 | 1035.479 | 1206.075 | 576.1757 | 4690.953 |
| 182 | 0.014124 | 0.25 | 8292 / 956 | 86.7 | 265.0142 | 169.3596 | 189.7605 | 352.0207 | 301.7579 | 1277.913 |
| 183 | -0.263149 | -3.14 | 8410 / 956 | 87.9 | 307.3528 | 337.1469 | 446.254 | 735.407 | 580.4351 | 2406.596 |
| 184 | 0.034096 | 0.46 | 8362 / 956 | 87.4 | 186.395 | 160.9434 | 218.0121 | 358.2736 | 280.5199 | 1204.144 |
| 185 | -0.00728 | -0.02 | 8115 / 956 | 84.8 | 209.3606 | 202.8116 | 280.095 | 463.2141 | 245.3091 | 1400.79 |
| 186 | -0.267516 | -3.18 | 7874 / 956 | 82.3 | 305.1782 | 354.1178 | 519.0316 | 787.9584 | 339.1406 | 2305.427 |
| 187 | -0.178385 | -2.16 | 7484 / 956 | 78.2 | 264.4392 | 281.426 | 339.0381 | 312.6648 | 189.749 | 1387.317 |
| 188 | -0.130134 | -1.56 | 7979 / 956 | 83.4 | 346.6856 | 224.0196 | 250.1593 | 329.3763 | 230.1504 | 1380.391 |
| 189 | -0.483449 | -5.83 | 8130 / 956 | 85 | 628.2807 | 703.6157 | 821.3253 | 1023.441 | 725.0945 | 3901.758 |
| 19 | -1.628065 | -20.23 | 6974 / 956 | 72.9 | 3389.606 | 3239.913 | 2522.763 | 1692.026 | 525.1065 | 11369.41 |
| 190 | -0.382561 | -4.65 | 7647 / 956 | 79.9 | 465.917 | 626.4025 | 684.5635 | 732.6541 | 409.5917 | 2919.129 |
| 191 | -0.451545 | -5.46 | 7399 / 956 | 77.3 | 565.414 | 672.8764 | 804.4835 | 859.0241 | 423.3889 | 3325.187 |
| 192 | -0.150519 | -1.78 | 7822 / 956 | 81.8 | 128.685 | 151.3588 | 269.7975 | 391.7842 | 353.7097 | 1295.335 |
| 193 | -0.365771 | -4.42 | 8284 / 956 | 86.6 | 517.0892 | 528.017 | 640.9317 | 910.0813 | 501.6963 | 3097.816 |
| 194 | -0.210788 | -2.55 | 7802 / 956 | 81.5 | 227.597 | 335.7213 | 420.5436 | 422.9744 | 288.5759 | 1695.412 |
| 195 | -0.388313 | -4.66 | 7452 / 956 | 77.9 | 490.9464 | 500.7963 | 623.5805 | 808.2322 | 457.5114 | 2881.067 |
| 196 | -0.296587 | -3.56 | 7856 / 956 | 82.1 | 351.9151 | 396.6224 | 521.4378 | 702.1099 | 369.6908 | 2341.776 |
| 197 | -0.183276 | -2.17 | 8302 / 956 | 86.8 | 160.2329 | 192.7511 | 335.8046 | 585.5516 | 352.9099 | 1627.25 |
| 198 | -0.098263 | -1.18 | 8149 / 956 | 85.2 | 234.9261 | 216.1986 | 171.5493 | 235.3665 | 154.5518 | 1012.592 |
| 199 | -0.471636 | -5.7 | 8384 / 956 | 87.6 | 689.9998 | 703.0416 | 808.6862 | 1010.393 | 725.4945 | 3937.615 |
| 2 | -0.275654 | -3.36 | 7923 / 956 | 82.8 | 428.156 | 479.6088 | 528.1867 | 629.9123 | 221.6576 | 2287.521 |
| 20 | -0.464306 | -5.71 | 7304 / 956 | 76.3 | 775.4624 | 859.6751 | 821.9051 | 620.6283 | 317.4775 | 3395.148 |
| 200 | -0.470971 | -5.69 | 8260 / 956 | 86.3 | 645.5637 | 721.6731 | 862.3292 | 1023.517 | 627.9204 | 3881.003 |
| 201 | -0.282188 | -3.36 | 8423 / 956 | 88 | 289.1153 | 353.9552 | 479.7082 | 788.8512 | 574.4338 | 2486.064 |
| 202 | -0.207981 | -2.51 | 8095 / 956 | 84.6 | 295.2785 | 314.4731 | 377.8447 | 504.8179 | 231.3495 | 1723.764 |
| 203 | -0.362509 | -4.39 | 7298 / 956 | 76.3 | 457.858 | 537.6634 | 589.3376 | 548.9297 | 488.9134 | 2622.702 |
| 204 | -0.555358 | -6.75 | 8117 / 956 | 84.8 | 859.5432 | 929.5586 | 963.3651 | 1085.506 | 645.0797 | 4483.053 |
| 205 | -0.037692 | -0.41 | 8356 / 956 | 87.3 | 180.2642 | 172.7785 | 221.6697 | 348.9315 | 254.1856 | 1177.83 |

Figure 5 cont.

| | Tot Dif | Tot Dif % | Valid | Valid % | Dif 1-6 | Dif 7-12 | Dif 13-18 | Dif 19-24 | Dif 25-30 | Dif - All |
|---|---|---|---|---|---|---|---|---|---|---|
| 206 | -0.14819 | -1.77 | 6951 / 956 | 72.6 | 209.357 | 245.0098 | 295.9403 | 294.1548 | 219.8 | 1264.262 |
| 207A | -0.102607 | -1.19 | 8378 / 956 | 87.6 | 167.2995 | 170.5582 | 195.0198 | 422.9273 | 396.118 | 1351.923 |
| 207B | -0.104125 | -1.21 | 8378 / 956 | 87.5 | 171.7425 | 172.1728 | 195.1673 | 424.6175 | 379.709 | 1343.409 |
| 208B | -0.030779 | -0.35 | 6730 / 956 | 70.3 | 170.3199 | 223.0398 | 358.9541 | 205.2462 | 134.4023 | 1091.962 |
| 209 | -0.161555 | -1.94 | 8049 / 956 | 84.1 | 184.3904 | 205.0305 | 279.657 | 380.9999 | 273.7571 | 1323.835 |
| 21 | -0.605935 | -7.4 | 7547 / 956 | 78.9 | 954.771 | 1022.208 | 1040.287 | 874.9514 | 655.3648 | 4547.562 |
| 210 | -0.223113 | -2.75 | 7157 / 956 | 74.8 | 445.6157 | 344.2335 | 440.4072 | 297.8935 | 93.32214 | 1621.472 |
| 211 | -0.44515 | -5.34 | 8237 / 956 | 86.1 | 575.4459 | 615.0755 | 746.9887 | 974.5655 | 753.2029 | 3665.278 |
| 212 | -0.105293 | -1.28 | 6855 / 956 | 71.6 | 181.1454 | 231.6925 | 232.6954 | 185.0289 | 114.8147 | 945.377 |
| 213 | 0.072503 | 0.91 | 8176 / 956 | 85.5 | 161.5685 | 217.4851 | 321.9677 | 482.4565 | 234.8909 | 1418.369 |
| 214 | -0.003419 | 0.03 | 7858 / 956 | 82.1 | 351.7736 | 239.3718 | 225.2363 | 434.2265 | 164.8073 | 1415.415 |
| 215 | -0.320926 | -3.88 | 7597 / 956 | 79.4 | 455.5044 | 499.3008 | 575.5158 | 586.5249 | 316.1666 | 2433.012 |
| 216 | -0.262098 | -3.12 | 8269 / 956 | 86.4 | 204.8111 | 231.6982 | 394.1475 | 778.5495 | 567.6569 | 2176.863 |
| 217 | -0.148425 | -1.72 | 8067 / 956 | 84.3 | 282.0401 | 253.5103 | 266.3283 | 502.1527 | 342.6979 | 1646.729 |
| 218 | -0.13341 | -1.59 | 7745 / 956 | 80.9 | 241.4601 | 218.8134 | 301.9991 | 333.4925 | 162.0329 | 1257.798 |
| 219 | -0.684343 | -8.31 | 8183 / 956 | 85.5 | 1022.078 | 1145.541 | 1226.087 | 1335.528 | 835.3927 | 5564.626 |
| 22 | -0.298849 | -3.59 | 8240 / 956 | 86.1 | 333.5053 | 424.8132 | 521.1881 | 744.9597 | 449.0616 | 2473.528 |
| 220 | -0.248756 | -3.01 | 8078 / 956 | 84.4 | 432.28 | 403.4119 | 424.1429 | 615.4443 | 414.4019 | 2289.681 |
| 221 | -0.47199 | -5.74 | 7594 / 956 | 79.4 | 662.0995 | 712.443 | 870.1394 | 970.3276 | 365.7722 | 3580.782 |
| 222 | -0.43487 | -5.19 | 8405 / 956 | 87.8 | 428.4016 | 540.3774 | 743.5869 | 1103.024 | 811.9096 | 3627.299 |
| 223 | -0.06434 | -0.76 | 7305 / 956 | 76.3 | 557.7872 | 412.0878 | 404.561 | 315.7839 | 85.356 | 1775.576 |
| 224 | 0.177441 | 2.25 | 8003 / 956 | 83.6 | 536.4201 | 488.036 | 334.96 | 302.6839 | 287.386 | 1949.488 |
| 225 | -0.282356 | -3.41 | 7916 / 956 | 82.7 | 334.6814 | 457.0697 | 579.5633 | 586.0499 | 408.8884 | 2366.253 |
| 226 | -0.341013 | -4.13 | 8153 / 956 | 85.2 | 498.164 | 535.6043 | 611.4746 | 674.542 | 440.9101 | 2760.695 |
| 227 | -0.412644 | -4.97 | 8253 / 956 | 86.3 | 539.0105 | 535.0008 | 662.2083 | 967.3274 | 671.5922 | 3375.139 |
| 228 | -0.200034 | -2.39 | 7863 / 956 | 82.2 | 448.8218 | 362.7536 | 375.6576 | 423.377 | 298.4649 | 1909.075 |
| 229 | -0.367731 | -4.49 | 8064 / 956 | 84.3 | 666.2577 | 629.9462 | 645.2321 | 732.2713 | 313.0054 | 2986.713 |
| 23 | 0.036822 | 0.57 | 8422 / 956 | 88 | 408.2303 | 328.5027 | 311.9628 | 564.9868 | 428.6128 | 2040.295 |
| 230 | -0.26975 | -3.26 | 8087 / 956 | 84.5 | 360.5171 | 428.3251 | 550.7145 | 596.3515 | 335.5626 | 2271.471 |
| 231 | -0.256122 | -3.14 | 7965 / 956 | 83.2 | 503.7757 | 507.7769 | 493.0597 | 417.4454 | 245.8121 | 2167.87 |
| 232 | -0.383996 | -4.72 | 7367 / 956 | 77 | 642.2456 | 684.0383 | 729.2047 | 553.1282 | 213.9999 | 2822.617 |
| 233 | -0.775273 | -9.48 | 7771 / 956 | 81.2 | 1244.211 | 1305.723 | 1365.835 | 1260.879 | 824.354 | 6001.001 |
| 234 | -0.579848 | -7.07 | 8025 / 956 | 83.9 | 1315.055 | 1522.976 | 1800.453 | 1511.148 | 428.899 | 6578.531 |
| 235 | -0.296251 | -3.64 | 7413 / 956 | 77.5 | 436.9614 | 494.4376 | 545.7515 | 497.8048 | 361.9306 | 2336.886 |
| 236 | -0.085294 | -0.95 | 8327 / 956 | 87 | 229.8415 | 237.7779 | 299.643 | 502.1388 | 317.3527 | 1586.754 |
| 237 | -0.334426 | -4.05 | 7851 / 956 | 82.1 | 479.9148 | 416.7686 | 522.0645 | 604.0356 | 585.1281 | 2607.912 |
| 238 | 0.119278 | 1.47 | 7998 / 956 | 83.6 | 279.2185 | 363.652 | 423.4276 | 539.1717 | 368.3109 | 1973.781 |
| 239 | -0.278335 | -3.39 | 7641 / 956 | 79.9 | 365.4766 | 474.2078 | 558.9313 | 517.4403 | 250.7428 | 2166.799 |
| 24 | -0.263753 | -3.17 | 7751 / 956 | 81 | 331.2794 | 376.7922 | 463.8012 | 558.1519 | 345.3794 | 2075.404 |
| 240 | -0.157167 | -1.81 | 8375 / 956 | 87.5 | 184.3294 | 168.8215 | 256.313 | 566.4208 | 479.8416 | 1655.726 |
| 241A | -1.005229 | -12.21 | 8288 / 956 | 86.6 | 1560.606 | 1621.985 | 1746.684 | 1984.076 | 1357.281 | 8270.633 |
| 241B | -1.024525 | -12.43 | 8416 / 956 | 88 | 1524.98 | 1670.031 | 1779.825 | 2068.913 | 1500.191 | 8543.94 |
| 242 | -0.394051 | -4.83 | 8070 / 956 | 84.3 | 657.0112 | 719.8514 | 728.2176 | 711.6113 | 394.2539 | 3210.945 |
| 243A | -0.118914 | -1.41 | 7712 / 956 | 80.6 | 398.6647 | 171.4754 | 291.2959 | 519.0797 | 181.5007 | 1562.016 |
| 243B | -0.060391 | -0.68 | 7414 / 956 | 77.5 | 359.1272 | 178.9736 | 308.8689 | 454.2262 | 147.6784 | 1448.874 |
| 244 | -0.785424 | -9.53 | 7689 / 956 | 80.4 | 1154.017 | 1233.048 | 1395.814 | 1453.879 | 778.1321 | 6014.89 |
| 245 | -0.240582 | -2.89 | 8109 / 956 | 84.3 | 355.8805 | 333.8887 | 372.2219 | 585.1107 | 297.4899 | 1944.592 |
| 246 | -0.48245 | -5.86 | 7794 / 956 | 81.5 | 628.3444 | 710.4834 | 845.4897 | 894.2689 | 647.8331 | 3726.42 |
| 247 | -0.357913 | -4.38 | 7488 / 956 | 78.3 | 550.9185 | 601.0605 | 654.1926 | 552.1145 | 316.3256 | 2674.612 |
| 248 | 0.017217 | 0.27 | 8072 / 956 | 84.4 | 202.1159 | 179.7163 | 173.7967 | 274.1326 | 197.2451 | 1027.007 |
| 249 | -0.48524 | -5.94 | 7684 / 956 | 80.3 | 827.9166 | 881.8004 | 885.2717 | 708.6642 | 415.2409 | 3718.894 |
| 25 | -0.369284 | -4.49 | 8174 / 956 | 85.4 | 563.948 | 809.9731 | 678.3997 | 814.4439 | 378.9338 | 3045.698 |
| 250 | -0.506614 | -6.2 | 7602 / 956 | 79.5 | 842.7302 | 851.2204 | 906.4619 | 777.1718 | 454.0295 | 3831.614 |
| 251 | -0.511676 | -6.2 | 8051 / 956 | 84.1 | 725.742 | 798.6307 | 903.5431 | 1075.14 | 615.1912 | 4118.247 |
| 252 | -0.208687 | -2.49 | 8263 / 956 | 86.4 | 308.6446 | 297.1351 | 347.5106 | 526.5828 | 372.2017 | 1852.075 |
| 253 | -0.523542 | -6.36 | 7591 / 956 | 79.3 | 716.9882 | 775.1416 | 878.1476 | 842.7372 | 731.7421 | 3944.757 |
| 254A | -0.544118 | -6.59 | 8232 / 956 | 86 | 774.9144 | 829.8829 | 913.823 | 1152.942 | 764.8109 | 4436.373 |
| 254B | -0.541906 | -6.56 | 8279 / 956 | 86.5 | 760.9394 | 827.0941 | 911.2646 | 1164.444 | 784.0644 | 4447.807 |
| 255 | -0.526484 | -6.38 | 7564 / 956 | 79.1 | 673.7763 | 744.6084 | 854.3823 | 845.6238 | 812.9975 | 3931.388 |
| 256 | -0.27536 | -3.36 | 7264 / 956 | 75.9 | 413.083 | 437.3042 | 515.5436 | 433.4119 | 203.9753 | 2003.318 |
| 257 | -0.416265 | -5.01 | 8371 / 956 | 87.5 | 466.3303 | 623.7138 | 754.8849 | 1004.15 | 625.0297 | 3474.108 |
| 258 | -0.104494 | -1.22 | 7219 / 956 | 75.4 | 133.2344 | 132.0325 | 169.6035 | 253.8478 | 328.5271 | 1017.245 |
| 259 | -0.558049 | -6.86 | 7267 / 956 | 76 | 1025.166 | 1019.103 | 884.9515 | 704.9776 | 412.472 | 4046.67 |
| 26 | -0.258737 | -3.06 | 8333 / 956 | 87.1 | 349.9351 | 240.883 | 397.3496 | 686.3211 | 610.539 | 2285.028 |

*Figure 5 cont.*

| | Tot Dif | Tot Dif % | Valid | Valid % | Dif 1-6 | Dif 7-12 | Dif 13-18 | Dif 19-24 | Dif 25-30 | Dif - All |
|---|---|---|---|---|---|---|---|---|---|---|
| 260 | -0.46472 | -5.63 | 8281 / 956 | 86.5 | 604.9028 | 706.9602 | 833.2761 | 1014.306 | 659.0461 | 3818.491 |
| 261 | -0.630168 | -7.71 | 7640 / 956 | 79.8 | 1028.26 | 1059.57 | 1112.334 | 950.7559 | 644.9729 | 4795.893 |
| 262 | -0.217601 | -2.59 | 8310 / 956 | 86.9 | 237.8502 | 296.8855 | 404.0306 | 602.2615 | 328.7626 | 1869.79 |
| 263 | -0.581163 | -7.04 | 8359 / 956 | 87.4 | 881.9817 | 924.5223 | 976.3321 | 1186.805 | 861.7562 | 4831.398 |
| 264 | -0.113254 | -1.29 | 8267 / 956 | 86.4 | 271.4248 | 209.8514 | 272.3073 | 496.691 | 405.0876 | 1655.362 |
| 265 | -0.189328 | -2.18 | 8368 / 956 | 87.5 | 324.0453 | 206.7183 | 377.375 | 835.5614 | 741.648 | 2485.348 |
| 266 | -0.023045 | -0.24 | 8194 / 956 | 85.6 | 223.8565 | 244.4019 | 305.0348 | 437.5192 | 232.2193 | 1443.032 |
| 267 | 0.09389 | 1.16 | 7451 / 956 | 77.9 | 200.1325 | 196.9617 | 208.9375 | 166.5372 | 119.7591 | 892.328 |
| 268 | -0.600116 | -7.33 | 7809 / 956 | 81.6 | 945.3278 | 1009.928 | 1086.478 | 1033.317 | 588.4948 | 4663.545 |
| 269 | 0.065939 | 0.87 | 8036 / 956 | 84 | 336.9103 | 257.494 | 214.3955 | 210.616 | 156.5057 | 1175.922 |
| 27 | -0.215085 | -2.56 | 8238 / 956 | 86.1 | 261.0682 | 265.805 | 382.2496 | 610.825 | 383.4697 | 1903.417 |
| 270 | -0.299302 | -3.57 | 8358 / 956 | 87.4 | 287.6283 | 356.0368 | 444.6185 | 746.2573 | 645.4359 | 2479.977 |
| 271 | -0.931677 | -11.35 | 8114 / 956 | 84.8 | 1471.065 | 1507.344 | 1653.301 | 1791.856 | 1090.843 | 7514.409 |
| 272 | -0.578118 | -6.99 | 7989 / 956 | 83.5 | 795.9956 | 887.0165 | 1002.946 | 1200.736 | 691.6723 | 4578.367 |
| 273 | -0.198091 | -2.36 | 7694 / 956 | 80.4 | 233.3479 | 271.8512 | 410.0765 | 582.1465 | 217.566 | 1714.988 |
| 274 | -0.540563 | -6.54 | 7962 / 956 | 83.2 | 702.2599 | 773.2389 | 933.139 | 1039.859 | 815.3809 | 4263.878 |
| 275 | -0.08823 | -1.06 | 7718 / 956 | 80.7 | 197.4399 | 202.9942 | 237.554 | 233.8068 | 159.8981 | 1031.693 |
| 276 | -0.096908 | -1.17 | 6494 / 956 | 67.9 | 172.7466 | 241.8482 | 244.9976 | 220.5406 | 92.95684 | 973.0898 |
| 278 | 0.160638 | 2.04 | 8031 / 956 | 83.9 | 490.0862 | 419.3041 | 377.5168 | 410.6533 | 205.4343 | 1902.995 |
| 279 | -0.275411 | -3.32 | 8282 / 956 | 86.6 | 361.0918 | 412.0381 | 506.9512 | 660.2371 | 362.8466 | 2303.165 |
| 28 | -0.070809 | -0.8 | 7863 / 956 | 82.2 | 162.2318 | 169.6173 | 252.9927 | 409.6031 | 276.8543 | 1271.299 |
| 280 | 0.012937 | 0.19 | 7081 / 956 | 74 | 250.6596 | 172.1297 | 229.4979 | 192.0431 | 100.8467 | 945.1769 |
| 281 | -0.206 | -2.46 | 8368 / 956 | 87.4 | 433.2235 | 293.8595 | 301.6959 | 523.7282 | 541.459 | 2093.966 |
| 29 | -0.490564 | -5.95 | 8000 / 956 | 83.6 | 737.4818 | 790.8383 | 834.0049 | 942.0553 | 588.4421 | 3892.822 |
| 3 | -0.412761 | -5.02 | 8274 / 956 | 86.5 | 668.7621 | 704.2998 | 748.2537 | 857.3828 | 438.8821 | 3417.581 |
| 30 | -0.490386 | -5.95 | 7997 / 956 | 83.6 | 736.388 | 789.9781 | 834.6906 | 943.7721 | 585.2101 | 3890.039 |
| 31 | -0.525888 | -6.41 | 8055 / 956 | 84.2 | 858.6169 | 857.8276 | 910.3405 | 998.4822 | 604.4244 | 4229.692 |
| 32 | -0.524937 | -6.4 | 8024 / 956 | 83.9 | 864.6668 | 860.2466 | 904.1209 | 993.5543 | 589.8862 | 4212.475 |
| 33 | -0.521942 | -6.32 | 7849 / 956 | 82 | 699.1186 | 816.5764 | 952.7439 | 902.0383 | 728.8273 | 4099.305 |
| 34 | -0.522656 | -6.33 | 7862 / 956 | 82.2 | 700.1172 | 816.935 | 953.5292 | 901.524 | 739.5305 | 4111.636 |
| 35 | -0.592803 | -7.18 | 8364 / 956 | 87.4 | 807.739 | 922.7264 | 1049.002 | 1275.498 | 868.4382 | 4923.404 |
| 36A | -0.40051 | -4.86 | 7163 / 956 | 74.9 | 500.0934 | 617.3195 | 588.3804 | 585.0562 | 563.3168 | 2854.166 |
| 36B | -0.401965 | -4.88 | 7193 / 956 | 75.2 | 511.7003 | 613.7582 | 587.551 | 593.2567 | 571.1155 | 2877.382 |
| 36C | -0.401261 | -4.87 | 7208 / 956 | 75.3 | 515.6558 | 616.123 | 590.7597 | 589.6071 | 566.7795 | 2878.925 |
| 37A | -0.055404 | -0.58 | 8335 / 956 | 87.1 | 239.1269 | 154.3691 | 168.0602 | 426.4446 | 388.8335 | 1376.834 |
| 37B | -0.052552 | -0.55 | 8259 / 956 | 86.3 | 214.7826 | 157.1131 | 179.3696 | 420.5094 | 344.0639 | 1315.839 |
| 37C | -0.015539 | -0.1 | 8188 / 956 | 85.6 | 248.7476 | 198.2408 | 190.0629 | 372.7193 | 293.2461 | 1303.017 |
| 38 | -0.63889 | -7.72 | 8333 / 956 | 87.1 | 917.1184 | 959.9086 | 1067.653 | 1352.17 | 979.9488 | 5276.799 |
| 39 | -0.63889 | -7.72 | 8333 / 956 | 87.1 | 917.1184 | 959.9086 | 1067.653 | 1352.17 | 979.9488 | 5276.799 |
| 4 | -0.405436 | -4.89 | 8245 / 956 | 86.2 | 524.4698 | 591.4101 | 691.7876 | 933.7513 | 590.9268 | 3332.346 |
| 40 | -0.188271 | -2.26 | 8422 / 956 | 88 | 336.6005 | 348.0051 | 410.9741 | 506.167 | 487.1247 | 2088.871 |
| 41 | -0.090935 | -1.05 | 7860 / 956 | 82.1 | 186.5143 | 121.2555 | 177.8401 | 335.7345 | 343.6978 | 1165.042 |
| 42 | 0.100775 | 1.26 | 8242 / 956 | 86.1 | 209.9788 | 219.6051 | 261.0747 | 270.7554 | 236.3303 | 1197.744 |
| 43 | -0.091334 | -1.14 | 7658 / 956 | 80 | 206.3237 | 202.8856 | 282.2227 | 374.204 | 213.5209 | 1279.157 |
| 44 | -0.562467 | -6.82 | 8032 / 956 | 83.9 | 827.3108 | 854.716 | 931.5258 | 1066.914 | 800.3073 | 4480.774 |
| 45 | -1.083838 | -13.33 | 8237 / 956 | 86.1 | 2220.608 | 2192.812 | 1914.748 | 1560.345 | 989.8043 | 8878.319 |
| 46 | -0.114185 | -1.3 | 7931 / 956 | 82.9 | 190.9434 | 154.0692 | 248.8625 | 429.7857 | 434.5723 | 1458.233 |
| 47 | -0.425745 | -5.12 | 8303 / 956 | 86.8 | 558.4829 | 600.0643 | 690.1492 | 958.2021 | 694.487 | 3501.386 |
| 48 | -0.004275 | 0.02 | 7656 / 956 | 80 | 263.2024 | 184.2098 | 238.5586 | 239.2418 | 210.0737 | 1135.286 |
| 49A | -0.300166 | -3.56 | 7259 / 956 | 75.9 | 153.5896 | 293.4982 | 576.3363 | 567.4989 | 723.3602 | 2314.283 |
| 49B | -0.298677 | -3.54 | 7289 / 956 | 76.2 | 154.5716 | 290.2271 | 591.2149 | 568.8733 | 715.9435 | 2320.83 |
| 5 | -0.401562 | -4.84 | 8219 / 956 | 85.9 | 499.4702 | 583.9352 | 690.3508 | 922.957 | 597.8215 | 3294.535 |
| 50 | -0.236125 | -2.83 | 7517 / 956 | 78.6 | 273.7518 | 303.5276 | 388.0606 | 427.8671 | 386.0729 | 1779.28 |
| 51 | -0.147843 | -1.82 | 7929 / 956 | 82.9 | 363.9748 | 343.8764 | 338.4603 | 426.3236 | 229.8559 | 1702.491 |
| 52A | -0.176701 | -2.11 | 7774 / 956 | 81.3 | 281.3954 | 241.309 | 311.8792 | 487.5004 | 255.5928 | 1577.677 |
| 52B | -0.177092 | -2.11 | 7800 / 956 | 81.5 | 281.095 | 241.8388 | 313.7905 | 487.3709 | 260.7067 | 1584.802 |
| 53A | -0.321077 | -3.92 | 7269 / 956 | 76 | 528.5127 | 544.4333 | 581.748 | 477.3406 | 216.4702 | 2348.505 |
| 53B | -0.332936 | -4.03 | 7539 / 956 | 78.8 | 529.6361 | 527.1541 | 589.6486 | 620.6964 | 250.4398 | 2517.575 |
| 54 | -0.24684 | -2.95 | 7710 / 956 | 80.6 | 230.3946 | 296.4731 | 416.2525 | 517.4399 | 442.4443 | 1903.004 |
| 55 | -0.493148 | -5.99 | 7647 / 956 | 79.9 | 727.1275 | 772.1274 | 867.3849 | 892.7681 | 495.9225 | 3755.33 |
| 56 | -0.371008 | -4.5 | 7754 / 956 | 81 | 537.2268 | 606.6057 | 713.1606 | 719.6427 | 316.5677 | 2893.203 |
| 57 | -0.659116 | -8.03 | 7965 / 956 | 83.2 | 975.6517 | 1054.166 | 1172.266 | 1156.625 | 854.0883 | 5212.797 |
| 58 | -0.45901 | -5.59 | 7510 / 956 | 78.5 | 687.1227 | 754.8116 | 832.8544 | 828.1801 | 330.7874 | 3433.756 |
| 59 | -0.442768 | -5.39 | 8058 / 956 | 84.2 | 698.8527 | 719.8777 | 837.9198 | 817.4026 | 481.1962 | 3555.249 |

Figure 5 cont.

|  | Tot Dif | Tot Dif % | Valid | Valid % | Dif 1-6 | Dif 7-12 | Dif 13-18 | Dif 19-24 | Dif 25-30 | Dif - All |
|---|---|---|---|---|---|---|---|---|---|---|
| 6 | -0.682917 | -8.38 | 7535 / 956 | 78.8 | 1127.891 | 1206.277 | 1216.555 | 958.3339 | 624.4414 | 5133.498 |
| 60 | -0.520111 | -6.28 | 8332 / 956 | 87.1 | 767.3917 | 788.1342 | 882.4245 | 1103.477 | 760.9336 | 4302.361 |
| 61 | -0.586016 | -7.1 | 8364 / 956 | 87.4 | 923.9808 | 938.8423 | 1020.553 | 1212.07 | 782.8941 | 4878.34 |
| 62 | -0.588407 | -7.2 | 7453 / 956 | 77.9 | 992.437 | 1001.508 | 983.3276 | 795.0182 | 581.9179 | 4354.209 |
| 63 | -0.522575 | -6.37 | 7666 / 956 | 80.1 | 720.0123 | 799.5923 | 953.6328 | 900.0373 | 606.7498 | 3980.024 |
| 64 | -0.483099 | -5.84 | 8356 / 956 | 87.3 | 644.646 | 730.6454 | 852.5755 | 1089.191 | 703.8993 | 4020.957 |
| 65 | -0.121819 | -1.48 | 7818 / 956 | 81.7 | 214.8836 | 209.5757 | 261.5364 | 283.1212 | 108.5816 | 1077.698 |
| 66 | -0.344834 | -4.11 | 8243 / 956 | 86.2 | 394.5008 | 454.2619 | 529.2754 | 814.9407 | 627.1426 | 2820.121 |
| 67 | -0.312717 | -3.76 | 8301 / 956 | 86.8 | 419.4761 | 472.628 | 564.0965 | 704.7172 | 446.0563 | 2606.974 |
| 68A | -0.480993 | -5.82 | 7682 / 956 | 80.3 | 585.5403 | 697.9411 | 820.6228 | 833.7534 | 726.708 | 3664.566 |
| 68B | -0.481534 | -5.83 | 7654 / 956 | 80 | 581.7476 | 702.8025 | 829.4313 | 832.7939 | 711.9641 | 3658.739 |
| 69 | -0.038857 | -0.45 | 7767 / 956 | 81.2 | 170.2543 | 142.4911 | 181.3761 | 254.6686 | 211.4987 | 960.2888 |
| 7 | -0.096619 | -1.12 | 7820 / 956 | 81.7 | 157.9318 | 122.2905 | 185.5124 | 298.6184 | 352.098 | 1116.451 |
| 70 | -0.369184 | -4.44 | 8093 / 956 | 84.6 | 460.5164 | 527.5341 | 645.3556 | 854.2532 | 482.894 | 2970.553 |
| 71 | -0.151004 | -1.82 | 8135 / 956 | 85 | 158.2448 | 240.6729 | 321.11 | 406.4311 | 186.0172 | 1312.476 |
| 72 | -0.579565 | -7.06 | 7881 / 956 | 82.4 | 855.186 | 895.2115 | 1003.868 | 1044.794 | 733.0377 | 4532.097 |
| 73 | -0.456279 | -5.54 | 7224 / 956 | 75.5 | 642.4617 | 714.5478 | 797.7102 | 720.7609 | 436.9003 | 3312.381 |
| 74 | -0.226468 | -2.73 | 7551 / 956 | 78.9 | 237.122 | 287.6832 | 420.7755 | 442.6094 | 329.9206 | 1718.111 |
| 75 | -0.606344 | -7.34 | 8257 / 956 | 86.3 | 678.6308 | 810.8764 | 1091.173 | 1503.871 | 879.2742 | 4963.826 |
| 76 | -0.323395 | -3.86 | 8214 / 956 | 85.8 | 410.6451 | 423.8485 | 625.4428 | 938.7228 | 550.6794 | 2949.338 |
| 77A | -0.127562 | -1.52 | 7930 / 956 | 82.9 | 133.591 | 144.6448 | 209.8384 | 320.1398 | 296.7777 | 1104.992 |
| 77B | -0.128105 | -1.52 | 7934 / 956 | 82.9 | 139.3241 | 144.9121 | 212.0553 | 306.4799 | 310.9052 | 1113.677 |
| 78 | -0.51744 | -6.3 | 7971 / 956 | 83.3 | 827.1857 | 858.2307 | 937.988 | 959.4507 | 535.2205 | 4118.075 |
| 79 | -0.324104 | -3.97 | 7210 / 956 | 75.4 | 472.494 | 532.6339 | 642.0849 | 538.8965 | 153.1663 | 2339.276 |
| 8 | -0.267257 | -3.18 | 8160 / 956 | 85.3 | 259.6726 | 323.8018 | 453.2216 | 699.6061 | 503.8256 | 2240.128 |
| 80 | -0.361015 | -4.37 | 8221 / 956 | 85.9 | 454.9714 | 498.4169 | 637.8261 | 887.9571 | 501.0489 | 2980.22 |
| 81 | 0.159492 | 1.99 | 7887 / 956 | 82.4 | 356.7838 | 347.4095 | 350.2039 | 306.3632 | 186.58 | 1547.34 |
| 82 | -0.16422 | -1.94 | 8175 / 956 | 85.4 | 193.297 | 162.1201 | 270.2264 | 507.1373 | 360.1533 | 1492.934 |
| 83 | -0.321337 | -3.94 | 8165 / 956 | 85.3 | 582.4363 | 615.9539 | 636.5464 | 620.965 | 355.9287 | 2811.83 |
| 84 | -0.675174 | -8.34 | 7229 / 956 | 75.6 | 1216.978 | 1257.384 | 1271.306 | 877.8983 | 289.8897 | 4913.456 |
| 85 | -0.14726 | -1.84 | 7567 / 956 | 79.1 | 539.4334 | 413.7697 | 516.7112 | 382.2513 | 189.7828 | 2041.948 |
| 86 | -0.177122 | -2.1 | 7033 / 956 | 73.5 | 254.0187 | 207.9115 | 275.6667 | 453.3543 | 354.9557 | 1545.907 |
| 87A | -0.026958 | -0.27 | 7877 / 956 | 82.3 | 221.1747 | 133.5736 | 201.0553 | 321.4314 | 247.8251 | 1125.06 |
| 87B | -0.019727 | -0.18 | 7873 / 956 | 82.3 | 285.4725 | 139.9856 | 207.0148 | 330.9795 | 254.3307 | 1217.783 |
| 88A | -0.213689 | -2.63 | 8053 / 956 | 84.2 | 440.3196 | 468.9856 | 489.3933 | 450.0253 | 208.288 | 2057.012 |
| 88B | -0.219706 | -2.71 | 8015 / 956 | 83.8 | 453.4286 | 473.4516 | 496.388 | 458.8273 | 202.2083 | 2084.304 |
| 89 | -0.085341 | -1.02 | 8145 / 956 | 85.1 | 169.2663 | 178.4557 | 262.4377 | 410.3161 | 247.296 | 1267.772 |
| 9 | -0.020555 | -0.18 | 8292 / 956 | 86.7 | 168.5058 | 146.0617 | 190.9128 | 358.6499 | 192.5922 | 1056.722 |
| 90 | 0.150861 | 1.88 | 8205 / 956 | 85.8 | 377.9344 | 351.9276 | 294.7762 | 304.2231 | 228.7557 | 1557.617 |
| 91 | -0.525018 | -6.36 | 8319 / 956 | 86.9 | 731.2701 | 763.6613 | 872.2645 | 1118.756 | 847.2792 | 4333.231 |
| 92A | -0.294878 | -3.64 | 7675 / 956 | 80.2 | 1008.617 | 1363.735 | 1313.559 | 1009.619 | 553.9556 | 5249.486 |
| 92B | -0.156671 | -1.91 | 8332 / 956 | 87.1 | 893.096 | 1194.625 | 1133.694 | 934.6063 | 611.5484 | 4767.57 |
| 93A | -0.441722 | -5.33 | 8286 / 956 | 86.6 | 557.4208 | 642.0901 | 785.6772 | 1028.571 | 623.5475 | 3637.306 |
| 93B | -0.439844 | -5.31 | 8302 / 956 | 86.8 | 549.9141 | 641.377 | 782.2634 | 1024.507 | 629.6345 | 3627.696 |
| 94 | -0.146578 | -1.72 | 8168 / 956 | 85.4 | 243.285 | 214.6879 | 357.944 | 505.9661 | 402.7466 | 1724.63 |
| 95 | -0.263664 | -3.14 | 8365 / 956 | 87.4 | 335.9843 | 397.1338 | 430.6254 | 633.8378 | 462.0106 | 2259.592 |
| 96 | -0.102801 | -1.23 | 8319 / 956 | 86.9 | 123.3198 | 150.1005 | 204.1485 | 353.6312 | 318.525 | 1149.725 |
| 97 | -0.589239 | -7.18 | 7628 / 956 | 79.7 | 896.6558 | 980.7056 | 1015.874 | 845.5941 | 719.8868 | 4458.716 |
| 98 | -0.299345 | -3.57 | 8221 / 956 | 85.9 | 298.6016 | 377.3631 | 485.4666 | 755.6858 | 530.5723 | 2447.689 |
| 99 | -0.909281 | -11.02 | 8283 / 956 | 86.6 | 1413.695 | 1421.564 | 1559.422 | 1859.474 | 1211.252 | 7465.406 |

*Figure 5 cont.*

CORNEAL BIOMETRY APPARATUS AND METHOD

PRIORITY CLAIM

This application is a United States national stage application of International Application No. PCT/AU2005/001386, filed on Sep. 12, 2005, which claims priority to, and the benefit of: (a) Australian Provisional Patent Application No. 2004905635, filed Sep. 29, 2004; and (b) U.S. Provisional Patent Application No. 60/685,484, filed May 31, 2005, and the entire contents of each of such applications are hereby incorporated by reference in their entirety.

FIELD OF THE INVENTION

The present invention relates broadly to a method and apparatus for validating the identity of a person by corneal imaging. The invention relates particularly, though not exclusively, to corneal topography for biometrics.

BACKGROUND

In the field of biometry, there are various techniques for validating the identity of a person. These techniques include facial recognition, fingerprint technology, iris scanning and retinal scanning. Facial recognition and fingerprint technology are generally well recognized in biometry but have inherent inaccuracies. With facial recognition, key indices of facial morphology are recorded digitally and stored on a database for future comparison. Weight loss or gain, changes in facial hair, cosmetic surgery or particular clothing worn for religious reasons that may partially cover the face, can render the technology unreliable. Facial recognition has at best a 95% reliability for identifying uniqueness.

Fingerprint technology has a long history in assisting with the solving of crime. Digital recording of fingerprint data relies on recording the miniature of fingerprints of subjects that may be kept on a database for later comparison. Fingerprint recognition becomes unreliable with five percent of the population having either congenitally blurred fingerprints or worn finger pads resulting from manual labor. These factors make fingerprint scanning potentially unreliable for a significant number of subjects when dealing with a large population. Civil libertarians are resistant to the holding and possible sharing of a database that can incriminate. Fingerprints can be obtained without consent and reproduced without the knowledge of the "owner" of the data.

Iris scanning has been available for around ten (10) years and involves—recording by means of photography some 250 or so features from the iris of the eye. The iris of the eye surrounds the central pupil, designed to expand and contract with variation in the light entering the pupil. As the pupil expands and contracts with variation in light levels or drugs of a class that may have a parasympathomimetic, parasympatholytic or sympathomimetic activity on the iris sphincter pupillae or dilator fibres, so then will the data change for the iris features. Iris data will also change as the pupil expands or contracts with variation in circulating adrenalin. This has limitations in the use of iris recognition systems, particularly out-doors in photopic conditions or indoors in scotopic conditions. Iris recognition performs reliably only in controlled illumination. Further, some racial groups have a perfectly smooth pigmented surface to the anterior iris surface lacking the Crypts of Fuch or iris naevi. Examples include a significant number of the indigenous Australians, New Zealand Maoris and Hawaiians. This causes an iris recognition system to be less reliable when screening such irides. The most optimistic of claims for iris recognition systems are around 94 to 99 percent accuracy—so for every 100 scans there will be at least one false match. This poses a significant problem for managing large databases where for example in a database of 60 million each person's scan will match 600,000 records in the database making it impossible to prevent someone claiming multiple identities. An iris scan can be obtained from up to one (1) meter away from the eye and thus there is opportunity to obtain data without consent.

With retinal scanning, the features of the optic nerve and retinal blood vessels are imaged to provide an excellent marker of uniqueness. However, acquiring this image requires clear media of the eye namely the cornea, lens and vitreous and a reasonable pupil size, typically at least 2.75 mm. This presents a problem when scanning eyes over the age of 60 years where, in the normal process of ageing, the clarity of the crystalline lens declines to ultimately form a cataract and the pupil becomes relatively smaller, commonly less than 2.5 mm, thus making the capture of a reliable image difficult and at times impossible. Whilst retinal scanning has high accuracy, capturing the data reliably poses a problem particularly in older age groups.

SUMMARY

According to one aspect of the present invention there is provided a method of validating the identity of a person, said method comprising the steps of:

capturing an image of at least part of a cornea of an eye of the person and deriving one or more geometric parameters for each of a plurality of points or areas across said part of the cornea;

comparing each of the geometric parameters derived from the person's cornea with corresponding reference geometric parameter for each of the points or areas of the cornea for that person; and validating the identity of the person based on the comparison of the geometric parameters for said points or areas.

Preferably the step of validating the identity of the person involves setting a cumulative maximum value for the difference in each of the geometric parameters on one occasion to another (or relative to the respective reference geometric parameter), and only validating the person when the sum of the difference of the parameter comparison for each of said points or areas is less than or equal to said maximum value. Alternatively the step of validating the identity of the person involves excluding potential matches when the cumulative maximum value for the difference in the geometric parameter is greater than a minimum value being the difference in the geometric parameters measured between the person on two temporally disparate occasions.

Preferably the step of capturing the image includes an arc step method wherein the vertex of the cornea is located from which a plurality of meridians are developed together with concentric rings, the plurality of points from which each of the geometric parameters is derived being defined by intersections of the meridians and rings. More preferably the concentric rings are at least in part a mire image of an illuminated and calibrated placido disc source and the concentric or mire rings are created by a mire image on the cornea utilizing the arc step method. Even more preferably the arc step method involves directing an infrared detector at the eye for accurate positioning of the corneal vertex or apex with respect to the placido or mire rings. The optical axis of said detector is aligned with the visual axis of the eye as the eye of the subject is fixed on a centrally located target geometrically coincident with the central locus of the placido or mire rings.

Alternately the step of capturing the image involves developing a plurality of cross-sections of the cornea corresponding to the plurality of areas of the cornea, and deriving the geometric parameter from each of the plurality of cornea cross-sections. Preferably the cross-sections are developed by directing a laser slit beam at the eye. Alignment of the optic axis of the image capture device and the visual axis of the eye may be facilitated by digital recording of the positioning of the anatomy of the iris and/or pupil with the subject eye fixated on a centrally located target with reference to the optic axis of the measuring device. Alignment may be maintained by means of software configured for superimposition of a pre-recorded image with a real-time image.

Preferably the method also comprises the step of grouping the plurality of points or areas into a plurality of zones together covering the imaged portion of the cornea. More preferably the step of comparing the geometric parameters includes the step of calculating the absolute differences between the geometric parameter derived and the corresponding reference geometric parameter for each of the plurality of points or areas for each of the zones, and summing the absolute differences for each of the zones wherein the summed absolute difference for the specified geometric parameter is compared with the cumulative maximum value for validation of the person.

Preferably the geometric parameter for the cornea includes axial radii (the curvature with respect to the axis of the keratoscope), tangential radii (the local curvature of the surface with reference to a tangential plane at that specified location), corneal height (the distance from the corneal surface to a given reference commonly a tangential plane normal to the corneal apex), refractive power (the power according to Snell's Law of a defined point on the corneal surface), corneal elevation (the distance from the corneal surface to a defined best fit sphere or curve), corneal slope (the angle in radians or degrees between the corneal surface and a tangential plane), corneal diameter (the length of a line from nasal limbus to temporal limbus where the line passes through the geometric centre of the cornea), a corneal chord (the length of a line from limbus to limbus but not passing through the geometric centre of the cornea) axial power (the power in dioptres calculated from the axial radius), tangential power (the power in dioptres calculated from the tangential radius) and/or corneal thickness (the distance from the corneal epithelium to the corneal endothelium either central, paracentral or peripheral).

Preferably the one or more geometric parameters includes a plurality of the geometric parameters.

Preferably the cumulative maximum value for comparison with the summed absolute difference for the geometric parameter of:

(i) axial radii is 400 mm;
(ii) tangential radii is 2000 mm; and/or
(iii) corneal height is 45 microns.

Preferably these cumulative maximum values are used when data is captured from a topographical image of the cornea using the arc-step method and up to 9,000 points on the cornea.

Preferably the method also comprises the step of weighting or factoring the parameter comparison prior to validation of the identity of the person. More preferably the step of comparing the geometric parameter involves filtering of the geometric parameter for each of the points or areas to retain only those geometric parameters within a preselected range. Even more preferably this weighting or factoring involves multiplying the summed absolute difference for the specified geometric parameter by the percentage of the plurality of points or areas retained.

Preferably the step of validating the identity of the person involves taking a selection of the plurality of geometric parameters for comparison, and only validating the identity of the person when the sum of the parameter comparison for each of said points or areas is less than respective of cumulative maximum values for all of said parameters.

According to another aspect of the invention there is provided an apparatus for validating the identity of a person, said apparatus comprising:

means for capturing an image of at least part of a cornea of an eye of the person, said imaging means being configured to derive one or more geometric parameters for each of a plurality of points or areas across said part of the cornea;

processing means in communication with the imaging means and being configured to compare each of the geometric parameters derived from the person's cornea with a corresponding reference geometric parameter for each of the points or areas of the cornea for that person; and validation means in communication with the processing means and being configured to validate the identity of the person based on the comparison of the geometric parameters for said points or areas.

Preferably said imaging means includes a video-imaging device servicing a video capture card of a central processing unit. More preferably said imaging means is a digital camera able to capture one or multiple digital images servicing the central processing unit, which includes a processor.

Preferably the imaging means includes an infra-red detector for alignment of the corneal vertex with said imaging means and visible light being adapted to be directed at the eye in the form of a placido disc illuminated and calibrated and according to an arc step method develop a plurality of meridians together with concentric rings or part thereof which when coincident create multiple points. More preferably the imaging means is a handheld device. Alternately the imaging means includes a laser being adapted to be directed at the eye to develop a plurality of cross-sections from which the geometric parameter is derived.

Preferably the processing means includes a reference database having the corresponding reference geometric parameter with which each of the geometric parameters is compared for each of the plurality of points or areas across the cornea.

BRIEF DESCRIPTION OF THE FIGURES

In order to achieve a better understanding of the nature of the present invention a preferred embodiment of a method and an apparatus for validating the identity of a person by corneal imaging will now be described, by way of example only, with reference to the accompanying representations in which:

FIG. 2 is a sample extract of sample data for a geometric parameter of a cornea for each of a variety of points such as those defined by the intersecting lines of FIG. 1.

FIG. 3 is an extract of a comparison of the summed absolute differences for a geometric parameter for groups of points or zones of the cornea data for the same person together with corresponding comparisons for other geometric parameters.

FIG. 4 is an extract for a similar comparison of geometric parameters for the cornea of one person against another.

FIG. 5 is an extract of a comparison of cumulative data for a geometric parameter for one person against corresponding geometric data for other persons.

DETAILED DESCRIPTION

Figure 1:
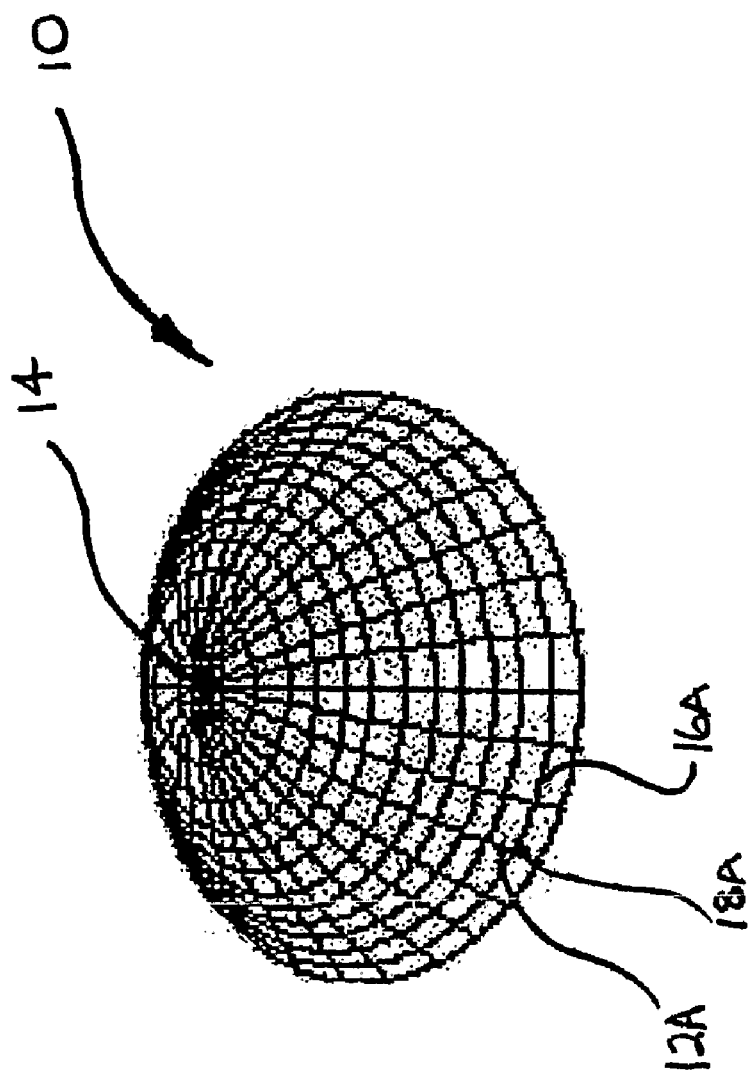
FIG. 1 is a schematic or perspective view of a cornea having been mapped or imaged according to an arc step method.

In a preferred embodiment of one aspect of the invention there is provided a method for validating the identity of a person using corneal imaging techniques. The method involves capturing an image of a person's cornea and where as illustrated in FIG. 1 the cornea is divided into a grid or map 10. The cornea grid or map 10 includes a plurality of meridians such as 12A extending from a vertex 14 of the cornea and being angularly equally separated. The grid or map 10 also includes a plurality of concentric rings such as 16A which are equally spaced and circumferentially separated intersecting with the meridians such as 12A at a plurality of points such as 18A. This method of corneal reconstruction is based on the arc step method and utilizes an infrared vertex detector (not shown).

In an alternate embodiment the cornea image is captured using laser technology taking a cross-section of the cornea utilizing a slit beam. This form of corneal topography is used in opthalmology to measure the eye prior to refractive surgery. U.S. Pat. Nos. 6,079,831, 6,120,150 and 6,257,723 each by Sarver et al disclose a device and method for this type of corneal topography using slit beam diffuse reflection system such as the Bausch & Lomb ORBSCAN topographer.

Figure 2:
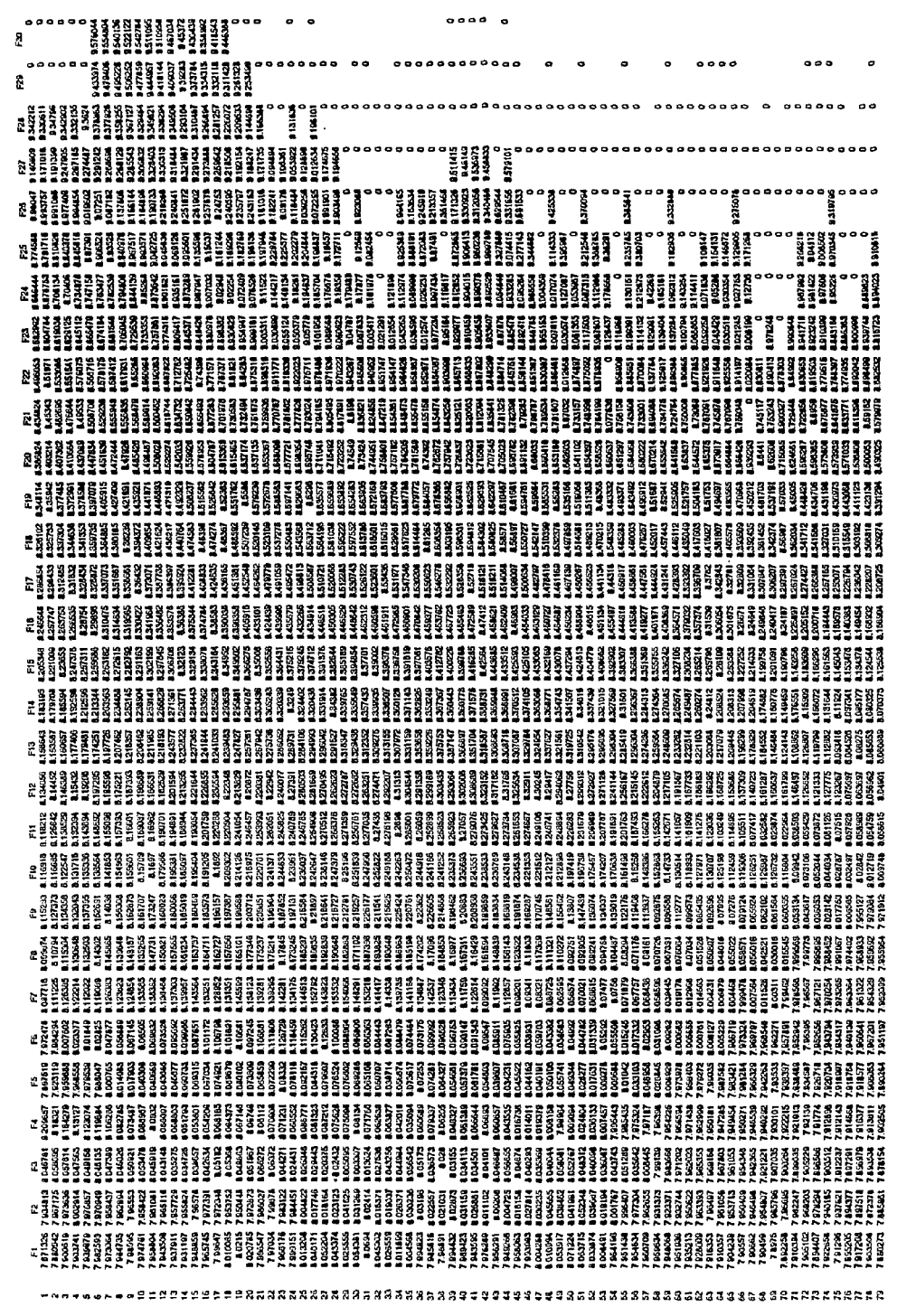
Figure 2:
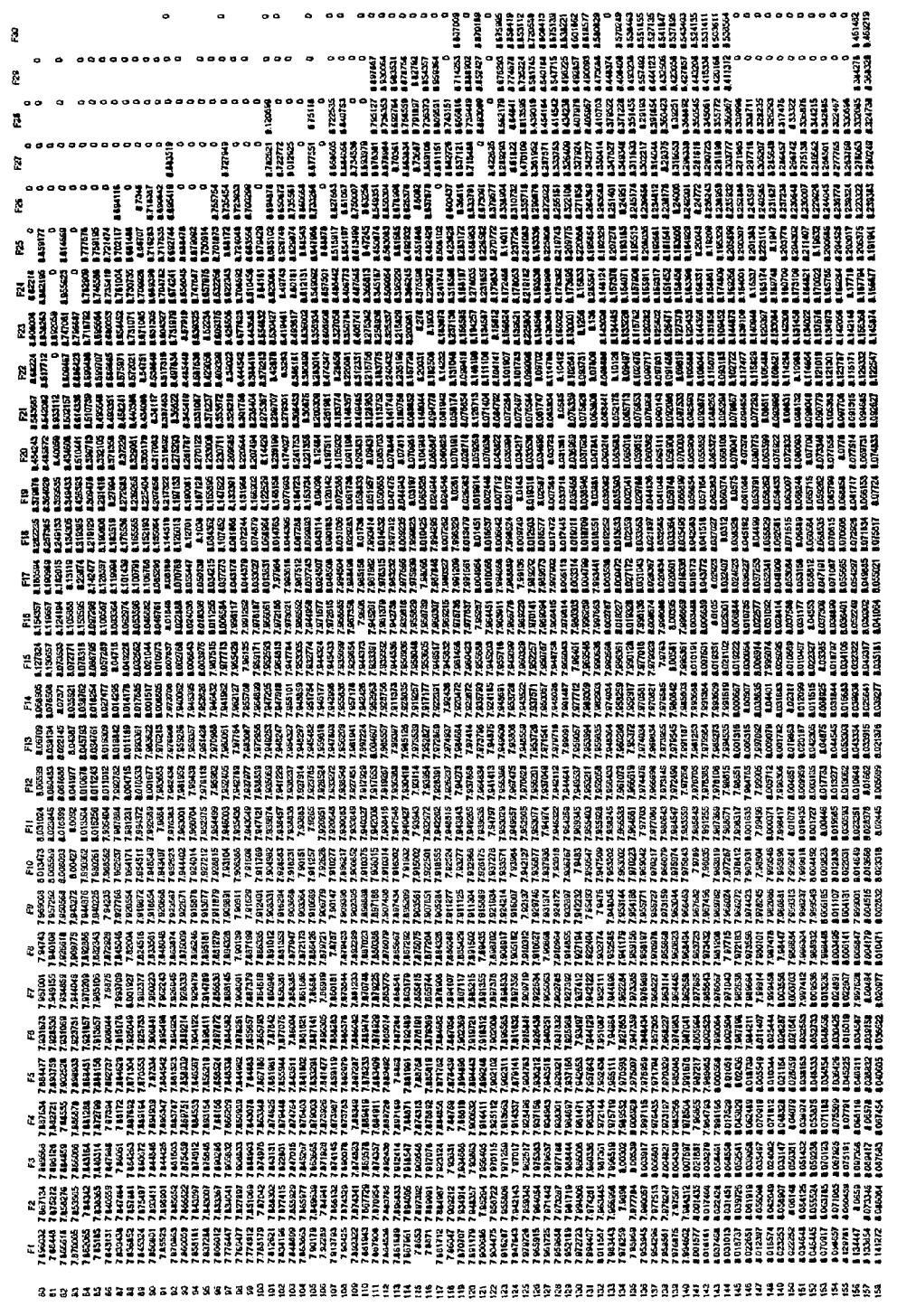
Figure 2:
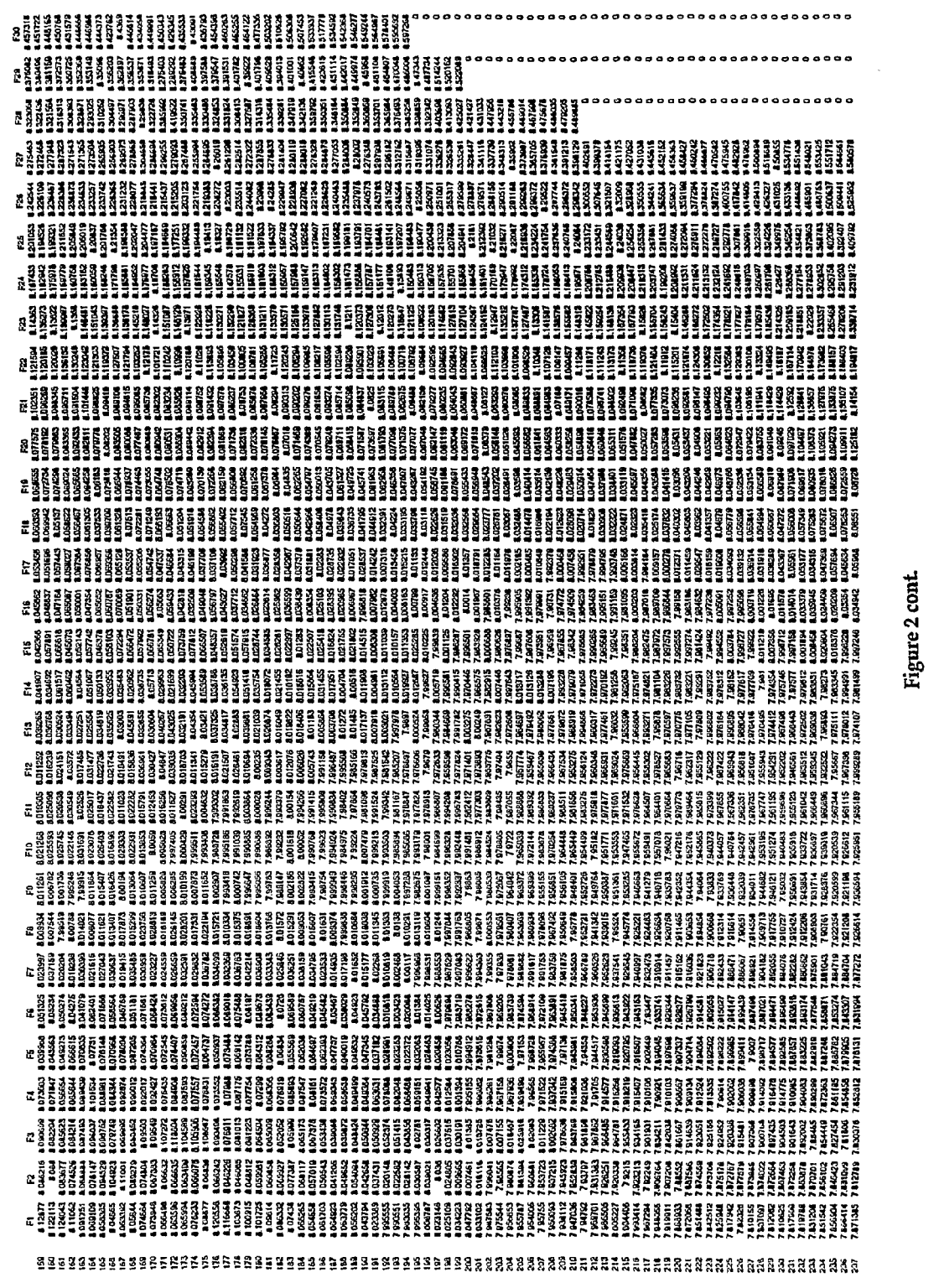
Figure 2:
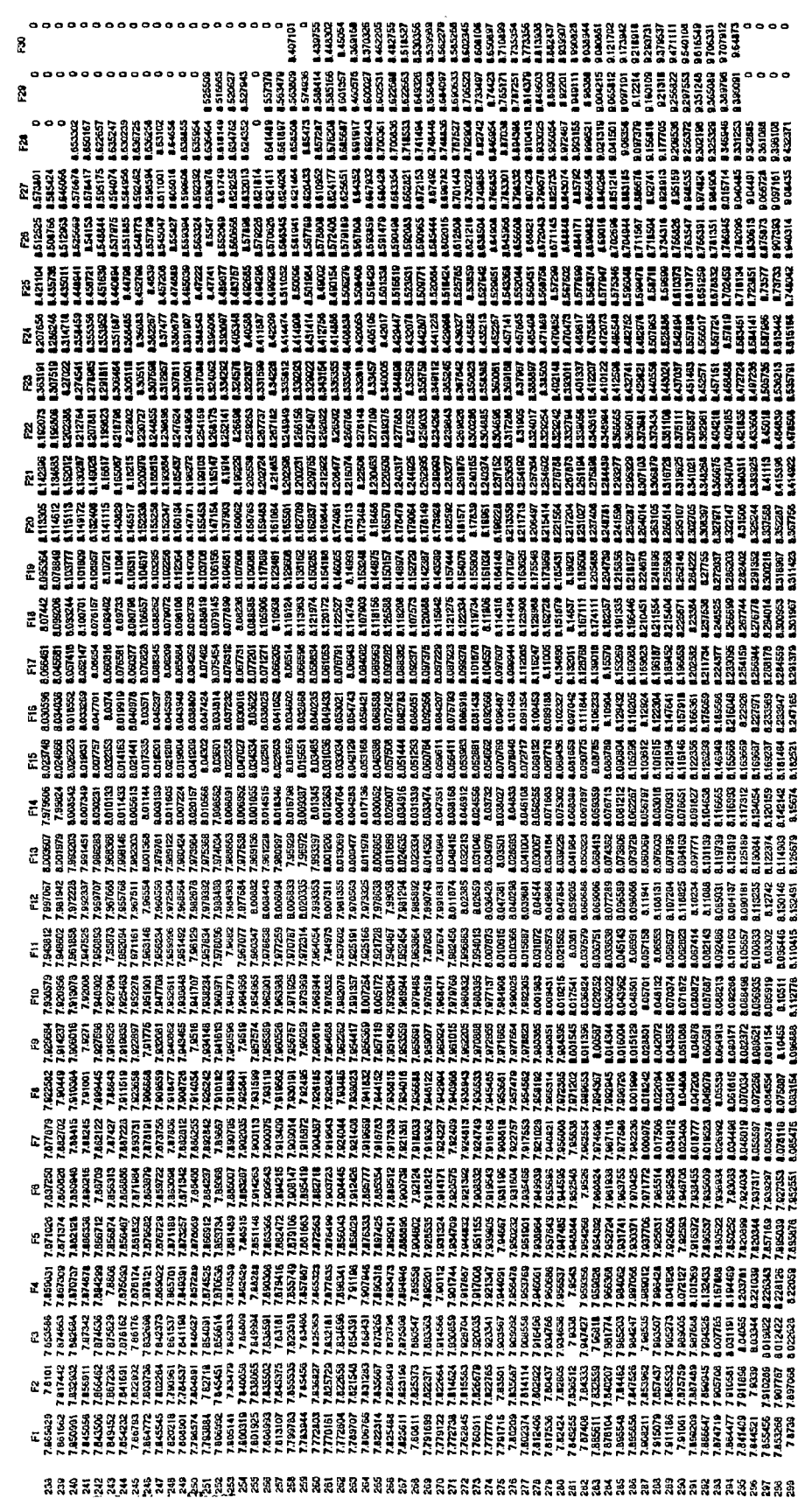

The preferred methodology then involves deriving one or more geometric parameters from the plurality of points mapped across the cornea. In this example the cornea map 10 includes around 300 meridians such as 12A and 30 rings such as 16A providing about 9,000 data points from which each of the geometric parameters is derived. The table of FIG. 2 illustrates raw data for these data points for the geometric parameter of axial radius with the rows 1 to 300 and columns F1 to F30 corresponding to the respective meridians such as 12A and concentric circles such as 16A of the corneal map of for example FIG. 1. Although not illustrated the drop down flag of "Data Type" provides data for other geometric parameters including tangential radius and corneal height.

FIG. 3 is a table illustrating comparison of the geometric parameters derived from the person's cornea of FIG. 2, in this example "113A" with "113B". This preferred methodology involves grouping the plurality of points of the cornea into a plurality of zones. In this example there are five (5) zones each consisting of six (6) concentric rings such as F1 to F6 of the table of FIG. 2.

The comparison of geometric parameters then involves:

1. calculating the absolute differences for each of the corresponding data points (in this case around 1,800 data points) for the zone; and
2. summing the absolute differences for each of the zones for that geometric parameter.

In the table of FIG. 3 rows five (5) to nine (9) headed "Abs. Diff (1-6)" to "Abs. Diff (25-30)" represent the calculated value of step 1 outlined above. For example, the addition of absolute differences for data points in the zone defined by F7 to F12 for axial radius is "27.74471714". The number in row ten (10) headed "Abs. Diff (All)" corresponds to the calculation of step 2 outlined above. For example, the sum of the cumulative value of the absolute differences for data points across all zones for the geometric parameter of axial radius is "228.4315422". The table of FIG. 3 shows corresponding numbers for other geometric parameters of the cornea including distance of each point from the visual axis "DST", corneal height "HGT", slope taken as tangent angle for each point "SLP" and tangential radius "TGL". The methodology also involves weighting or factoring of the comparison dependent on the percentage or number of data points retained. For example, as shown in the table of FIG. 3, the geometric parameter of axial radius "AXL" retained 8,283 data points of a total of 9,568 data points as shown in row 3 headed "Valid". As a percentage this represents 86.6% which in row 4 of the table is shown as the "Valid (%)".

Importantly, this comparison of the geometric parameter, such as axial radius allows for validation of the identity of the person. In this embodiment it has been revealed that the corneal comparison of for example the geometric parameters of the table of FIG. 3 associates like with like when the sum of the parameter comparison, such as the "Abs. Diff (All)", is less than a cumulative maximum value. In the case of the axial radius it has been revealed that a cumulative maximum value for axial radii of around 400 mm is effective in identifying like with like. Although it will be appreciated that the parameter comparison data of FIG. 3 is merely illustrative, it has also been revealed that cumulative maximum values for tangential radii and corneal height of about 2,000 mm and 45 microns, respectively, are similarly effective in identifying like with like.

The table of FIG. 4 shows the results when "113A" is compared with another person in this case "114". The cumulative comparison for each of the geometric parameters reveals a number greater then the respective cumulative maximum values and as such identifies a "mismatch of cornea data confirming that the persons are not the same.

FIG. 5 is a table comparing the geometric parameter of the axial radii for "113A" with corresponding data for cornea of other persons. It is significant to note that in the final column headed "Dif-All" representing the sum of the absolute differences for each of the zones, no value is less than the cumulative maximum value of 400 except for the other data for "113B" and "113C" in rows 17 and 18 respectively of this table. This confirms that the chosen cumulative maximum value for the axial radii of 400 mm is effective in validating or identifying like with like. Similarly, the applicant has empirically derived from a large number of comparisons that the chosen cumulative maximum values for the geometric parameters of tangential radii and corneal height are effective in identifying like with like.

The sensitivity may be improved by weighting data from certain parts/areas of the cornea. For example, "additional" weighting may be given to the mid-peripheral nasal region of the cornea. Where data across the cornea is not weighted there is a difference of the like to unlike of around 400%, weighting may increase the difference from like to unlike of around 1600% (or an increase in sensitivity of 4 times). This weighting may reduce the number of recognized data points from around 9,000 points to 200-300 points.

The accuracy of this methodology may also be improved by relying upon a combination of the geometric parameters before validating the identify of a person. For example, the method may require that the corneal comparison for the parameters of axial radii, tangential radii and corneal height are all less than the respective cumulative maximum value of 400 mm, 2,000 mm and 45 microns.

Figure 6:
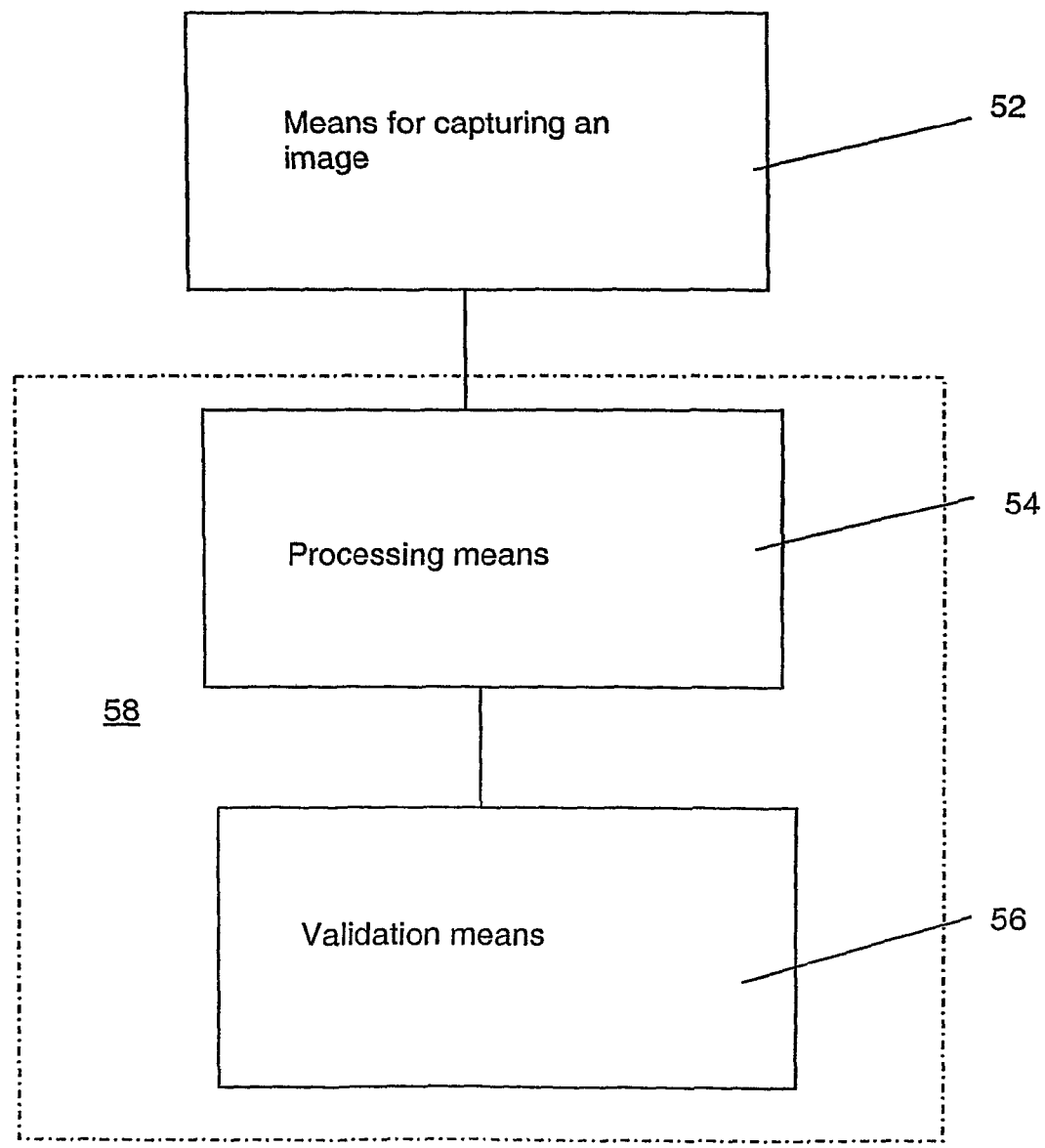
FIG. 6 is a schematic of an embodiment of an apparatus for validating the identity of a person by corneal imaging.

FIG. 6 is a schematic representation of an embodiment of an apparatus for validating the identity of a person. The apparatus depicted generally as 50 includes means for capturing an image 52 in communication with processing means 54 and validation means 56. The imaging means 52 may be in the form of a corneal topographer such as that relying upon arc step corneal reconstruction or the ORBSCAN device disclosed earlier. In yet another example and as disclosed in U.S. Pat. Nos. 5,512,965 and 5,512,966 each by Snook, the imaging means includes a video camera configured to record slit light beam images which are processed in a digital format to produce a corneal curvature profile and corneal thickness profile. The imaging means may also be in the form of a digital camera, mobile or cell phone, or Personal Digital Assistant (PDA) or a dedicated wall or desk mounted device for mass processing of subjects exiting or entering a building.

The processing means and validation means of this embodiment may be in the form of a microprocessor or processor 58 configured to compare the geometric parameters and validate the person based on a cumulative maximum value for one or more types of geometric parameters. The processor 58 includes a reference database having corresponding reference geometric parameters with which the comparison is made as described in the preferred methodology of the invention. The processor 58 may also include a validation database having the cumulative maximum value for each of the geometric parameters.

An alternative embodiment of the invention utilizes two thousand five hundred points representing discrete data points derived from the corneal map generated by the mire image of the placido disc illuminated and calibrated and combined with the arc step method thus rendering an array of points which are evenly and uniformly distributed across the corneal surface. The data points can be arranged in an array or matrix of cells being fifty cells wide by fifty cells high. In this embodiment when one cornea is compared to another the absolute difference is calculated for corresponding cells in each array. The cornea is divided into three zones corresponding to lines one to fifteen in the matrix thence lines sixteen to thirty five and thence lines thirty-six to fifty. The absolute sum difference between corresponding zones for the corneae is calculated. Where a null or zero value occurs within the boundaries of the number matrix of an array a value is attributed to that cell as a calculated value dependent on the value of immediately surrounding cells in the array. Further, when a real value occurs in the number matrix of one array and a zero or null value occurs in the corresponding cell of the compared array the value for both cells is recorded as zero. This may occur with lid interference or shadows from the cilia of the eye occurring more in one array than the other thus interfering with the mire image of the placido rings. The percentage of cells in each array returning a null or zero value is recorded and the value of cells returning real values is calculated. The absolute sum difference for each zone is given weighting by dividing the absolute sum difference by the percentage of cells with real values expressed as a decimal number (where for example 81% becomes 0.81). If using corneal height the absolute sum difference between corresponding zones of two corneae being compared is 25.04030650 microns and 81.2% of cells in corresponding arrays returned real values then the weighted (or corrected) difference is 30.83781589.

In this embodiment the corneal data consisting of two thousand five hundred discrete data points is divided into three zones being lines one to fifteen and lines sixteen to thirty five and lines thirty six to fifty. When one corneal data set (the subject) is compared to a large database of many client eyes the client eye from the database with the least weighted sum difference for each zone of the cornea is recorded. That client eye with the least weighted sum difference is awarded a score of 'four' (4) for zones corresponding to lines one to fifteen and sixteen to thirty five and for least weighted sum difference for all three zones (one to fifteen, sixteen to thirty five and thirty six to fifty).

That client eye with next least weighted sum difference is awarded a score of three (3) in the same manner as above, the next client eye with the least weighted sum difference is awarded a score of two (2) in the same manner as above and the next client eye with the least weighted sum difference is awarded a score of one (1) in the same manner as above. The next closest matches whilst listed in order from closest to least close match, attract a score of zero (0).

In this embodiment the scores are summed whereby two parameters are used for comparison being corneal height and axial radius.

In this embodiment a subject's corneal data can be compared to a database whereby the subject has a pre-recorded dataset and when compared to that database of many different corneal datasets the dataset belonging to the subject on the database should result in having the least difference to the subject's dataset and therefore the highest score. In this embodiment the scores are ranked highest to lowest. The highest score when making a match also for name confirms the subject is recognized as belonging to the database and therefore as a match for the subject eye.

In one application, the corneal data of a subject can be recorded on a card capable of retention of digital data by means of a computer chip or magnetic strip. Imaging means such as a topographic device can be used to capture the subject's corneal data for comparison from one occasion to another against their recorded corneal data on the card. The subject's card is scanned by a scanning device which communicates with the topographic device to allow for corneal data comparison. The topographic device (or other imaging means) or an associated device includes a processor which confirms ownership of the card and access can be granted or with-held subject to confirmation that the data recorded on the card passes the necessary criteria to be a match to the corneal data of the subject as captured by the imaging means.

In another application, the imaging means or data capture device communicates with a remote database which holds a dataset of corneal geometric parameters for various individuals. The data capture device or an associated device may include or communicate with switching means which on verification of the subject provides access for that person. Access can be granted or denied to secure areas of the built environment, access to a mobile phone or Personal Digital Assistant (PDA) device, access to a personal computer or computer network, access to a banking network by way of an automatic teller machine, access to a motor vehicle or access to any device, area, computer terminal, or machine requiring a secure application to defend against unwanted intrusion or unauthorized use.

In a further application, corneal data may be recorded on a credit card or smart card. Ownership of the credit card or smart card can be confirmed by instantaneous comparison of the credit card or smart card corneal data with captured corneal data (using imaging means) of the holder of the credit card or smart card.

The method and apparatus of the preferred embodiment may have other various biometric applications including limited access when secure borders are required in the workplace or built environment, verification of credit card users, and other security or for example military related applications. For example, passports may be embedded with corneal data against which scanned or imaged corresponding data is compared for validation. The method and apparatus may be utilized in the securing of military hardware, or in providing limited and secure access to for example digital files such as those attached to emails. In the embodiment described and for example using the combination of three (3) selected geometric parameters, it is estimated that approximately only one in 15 billion people will be incorrectly identified as like with like.

Now that a preferred embodiment of the present invention has been described in some detail it will be apparent to those skilled in the art that the method and apparatus for validating the identity of a person by corneal imaging has the following advantages over the admitted prior art:

1. the technique provides a particularly reliable and accurate method of confirming like with like;

2. the apparatus or biometric tool is relatively safe and inexpensive and generally can only be used with the consent of those upon which it is utilized;

3. the method can be utilized on a broad range of people not limited to any particular age group provided an effective cornea image can be taken.

Those skilled in the art will appreciate that the invention described herein is acceptable to variations and modifications other than those specifically described. For example, the method may not be restricted to the geometric parameters discussed but rather may extend to other geometric parameters which on comparison with corresponding base parameters for the same person are effective in verifying that person's identity or uniqueness. All such variations and modifications are to be considered within the scope of the present invention the nature of which is to be determined from the foregoing description.

It is to be understood that any acknowledgment of prior art in this patent specification is not to be taken as an admission that this prior art forms part of the common general knowledge in the relevant art.

The invention claimed is:

1. A method of validating the identity of a person, said method comprising the steps of:
    capturing an image of at least part of a cornea of an eye of the person and deriving one or more geometric parameters for each of a plurality of points or areas across said part of the cornea;
    comparing each of the geometric parameters derived from the person's cornea with a corresponding reference geometric parameter for each of the points or areas of the cornea for that person; and
    validating the identity of the person based on the comparison of the geometric parameters for said points or areas.

2. A method of validating the identity of a person as claimed in claim 1, wherein the step of validating the identity of the person involves setting a cumulative maximum value for the difference in each of the geometric parameters on one occasion to another, and only validating the person when the sum of the difference of the parameter comparison for each of said points or areas is less than or equal to said maximum value.

3. A method of validating the identity of a person as claimed in claim 2, wherein the step of validating the identity of the person involves taking a selection of the geometric parameters for comparison, and only validating the identity of the person when the sum of the parameter comparison for each of said points or areas is less than respective of cumulative maximum values for all of said parameters.

4. A method of validating the identity of a person as claimed in claim 2, wherein the step of validating the identity of the person involves awarding a predetermined highest score to a least weighted sum difference based on corneal points, areas and/or the total area of imaged cornea, and confirming a matching identity when a comparison of corneal dataset and name or personal identification number with a database of same matches the predetermined highest score with same name or personal identification number.

5. A method of validating the identity of a person as claimed in either of claims 1 or 2 wherein, the step of capturing the image includes an arc step method wherein a vertex of the cornea is located from which a plurality of meridians are developed together with concentric rings, the plurality of points from which each of the geometric parameters is derived being defined by intersections of the meridians and rings.

6. A method of validating the identity of a person as claimed in claim 5, wherein the image capture involves directing an infrared detector at the eye for alignment of the vertex distance of said detector with the corneal apex and a mechanism for alignment of the optic axis of the device with the visual avis of the eye.

7. A method of validating the identity of a person as claimed in either of claims 1 or 2, wherein the step of capturing the image involves developing a plurality of cross-sections of the cornea corresponding to the plurality of areas of the cornea, and deriving the geometric parameter from each of the plurality of cornea cross-sections.

8. A method of validating the identity of a person as claimed in claim 7, wherein the cross-sections are developed by directing a laser at the eye.

9. A method of validating the identity of a person as claimed in any one of claims 1 to 4 also comprising the step of grouping the plurality of points or areas into a plurality of zones together covering the imaged portion of the cornea.

10. A method of validating the identity of a person as claimed in claim 9, wherein the step of comparing the geometric parameters includes the step of calculating the absolute differences between the geometric parameter derived and the corresponding reference geometric parameter for each of the plurality of points or areas for each of the zones, and summing the absolute differences for each of the zones wherein the summed absolute difference for the specified geometric parameter is compared with the cumulative maximum value for validation of the person.

11. A method of validating the identity of a person as claimed in any one of the preceding claims, wherein the geometric parameter for the cornea includes axial radii, tangential radii, corneal height, corneal elevation, refractive power, axial power, tangential power, corneal thickness, corneal diameter, or a corneal chord.

12. A method of validating the identity of a person as claimed in claim 11, wherein the geometric parameter is a plurality of the geometric parameters.

13. A method of validating the identity of a person as claimed in either of claim 11 or 10, wherein the cumulative maximum value for comparison with the summed absolute difference for the geometric parameter of:
    (i) axial radii is 400 mm;
    (ii) tangential radii is 2000 mm; and/or
    (iii) corneal height is 45 microns.

14. A method of validating the identity of a person as claimed in claim 13, wherein the cumulative maximum value is used when data is captured from a topographical image of the cornea using the arc step method and up to 9,000 points on the cornea.

15. A method of validating the identity of a person as claimed in any one of the preceding claims also comprising the step of weighting or factoring the geometric parameter comparison prior to validation of the identity of the person.

16. A method of validating the identity of a person as claimed in claim 15, wherein the step of comparing the geometric parameter involves filtering of the geometric parameter for each of the points or areas to retain only those geometric parameters within a preselected range.

17. A method of validating the identity of a person as claimed in claim 16, wherein the weighting or factoring involves multiplying the summed absolute difference for the specified geometric parameter by the percentage of the plurality of points or areas retained.

18. An apparatus for validating the identity of a person, said apparatus comprising:
means for capturing an image of at least part of a cornea of an eye of the person, said imaging means being configured to derive one or more geometric parameters for each of a plurality of points or areas across said part of the cornea;
processing means in communication with the imaging means and being configured to compare each of the geometric parameters derived from the person's cornea with a corresponding reference geometric parameter for each of the points or areas of the cornea for that person; and
validation means in communication with the processing means and being configured to validate the identity of the person based on the comparison of the geometric parameters for said points or areas.

19. An apparatus for validating the identity of a person as claimed in claim 18 wherein said imaging means includes a video-imaging device servicing a video capture card of a central processing unit.

20. An apparatus for validating the identity of a person as claimed in claim 19 wherein said imaging means is a digital camera able to capture one or multiple digital images servicing the central processing unit which includes a processor.

21. An apparatus for validating the identity of a person as claimed in claim 18, wherein the imaging means includes an infra-red detector for vertex alignment of said imaging means and visible light being adapted to be directed at the eye and according to an arc step method develop a plurality of meridians together with concentric rings or part thereof.

22. An apparatus for validating the identity of a person as claimed in any one of claims 18 to 21, wherein the imaging means is a handheld device.

23. An apparatus for validating the identity of a person as claimed in any one of claims 18 to 22, wherein the imaging means includes a laser being adapted to be directed at the eye to develop a plurality of cross-sections from which the geometric parameter is derived.

24. An apparatus for validating the identity of a person as claimed in any one of claims 18 to 23, wherein the processing means includes a reference database having the corresponding reference geometric parameter with which each of the geometric parameters is compared for each of the plurality of points or areas across the cornea.

25. An apparatus for validating the identity of a person as claimed in any one of claims 18 to 24, wherein the validation means includes a validation database having a cumulative maximum value for each of the geometric parameters, the validation means being configured to only validate the person when the sum of the parameter comparison for each of the points or areas is less than said maximum value.

26. An apparatus for validating the identity of a person claimed in any one of the claims 18 to 23 wherein the validation means includes scoring means being configured to award a predetermined highest score to a least weighted sum difference based on corneal points, areas and/or the total area of imaged cornea, the validation means confirming a matching identity when a comparison of corneal dataset and name or personal identification number with a database of same, matches the predetermined highest score with same name or personal identification number.

* * * * *